US009226803B2

(12) United States Patent
Cosse et al.

(10) Patent No.: US 9,226,803 B2
(45) Date of Patent: Jan. 5, 2016

(54) ORTHODONTIC APPLIANCE SYSTEMS

(75) Inventors: Christopher C. Cosse, Shreveport, LA (US); Christopher W. LaBorde, Nashville, TN (US)

(73) Assignee: Christopher C. Cosse, Shreveport, LA (US)

(*) Notice: Subject to any disclaimer, the term of this patent is extended or adjusted under 35 U.S.C. 154(b) by 546 days.

(21) Appl. No.: 13/012,116

(22) Filed: Jan. 24, 2011

(65) Prior Publication Data
US 2011/0183280 A1 Jul. 28, 2011

Related U.S. Application Data

(60) Provisional application No. 61/434,946, filed on Jan. 21, 2011, provisional application No. 61/297,870, filed on Jan. 25, 2010.

(51) Int. Cl.
*A61C 3/00* (2006.01)
*A61C 7/28* (2006.01)
*A61C 7/14* (2006.01)

(52) U.S. Cl.
CPC ...... *A61C 7/28* (2013.01); *A61C 7/14* (2013.01); *A61C 7/285* (2013.01); *A61C 7/287* (2013.01)

(58) Field of Classification Search
CPC .............. A61C 7/00; A61C 7/12; A61C 7/14; A61C 7/141; A61C 7/143; A61C 7/145; A61C 7/148; A61C 7/16; A61C 7/22; A61C 7/28; A61C 7/285; A61C 7/287; A61C 7/30; A61C 7/303
USPC .................. 433/2, 8, 10, 11, 13, 14, 18, 24
See application file for complete search history.

(56) References Cited

U.S. PATENT DOCUMENTS

| | | | |
|---|---|---|---|
| 2,908,974 A | | 10/1959 | Stifter |
| 2,959,856 A | | 11/1960 | Gurin |
| 3,262,207 A | | 7/1966 | Kesling |
| 3,683,502 A | | 8/1972 | Wallshein |
| 4,212,638 A | | 7/1980 | Korn |
| 4,249,897 A | | 2/1981 | Anderson |
| 4,299,569 A | * | 11/1981 | Frantz .............................. 433/8 |
| 4,302,532 A | | 11/1981 | Wallshein |
| 4,353,692 A | | 10/1982 | Karrakussoglu |
| 4,373,914 A | | 2/1983 | Colbert |
| 4,583,944 A | | 4/1986 | Hanson |
| 4,597,739 A | | 7/1986 | Rosenberg |

(Continued)

*Primary Examiner* — Cris L Rodriguez
*Assistant Examiner* — Matthew Nelson
(74) *Attorney, Agent, or Firm* — Dascenzo Intellectual Property Law, P.C.

(57) ABSTRACT

Orthodontic appliance systems including self-ligating orthodontic brackets and/or orthodontic brackets that include a prescription-altering insert that is configured to be removably coupled to the bracket. The prescriptive insert may be optional in some embodiments. In some embodiments, the prescriptive insert may define and/or alter the prescription of the bracket, such as a prescription defined by the bracket when the insert is not utilized. A plurality of prescriptive inserts may be provided, with each insert defining a unique orthodontic prescription when coupled to the bracket. In some embodiments, the bracket is a self-ligating bracket that includes a base and a repositionable closure for selectively obstructing an opening in an archwire passage of the bracket. In some embodiments, the closure defines more than one side, or wall, of the archwire passage and/or is pivotally coupled to the base by a floating hinge or other displaceable positioning mechanism.

31 Claims, 15 Drawing Sheets

(56) References Cited

U.S. PATENT DOCUMENTS

| | | | |
|---|---|---|---|
| 4,850,865 A * | 7/1989 | Napolitano | 433/8 |
| 5,044,945 A | 9/1991 | Peterson | |
| 5,224,858 A | 7/1993 | Hanson | |
| 5,597,302 A * | 1/1997 | Pospisil et al. | 433/8 |
| 5,993,207 A | 11/1999 | Spencer | |
| 6,071,118 A | 6/2000 | Damon | |
| 6,168,429 B1 | 1/2001 | Brown | |
| 6,193,509 B1 | 2/2001 | DeVincenzo | |
| 6,217,324 B1 | 4/2001 | Kesling | |
| 6,264,469 B1 | 7/2001 | Moschik | |
| 6,595,774 B1 | 7/2003 | Risse | |
| 6,939,133 B2 | 9/2005 | Voudouris | |
| 7,025,591 B1 | 4/2006 | Kesling | |
| 7,063,531 B2 | 6/2006 | Maijer et al. | |
| 7,153,130 B2 | 12/2006 | Christoff | |
| 7,214,057 B2 | 5/2007 | Voudouris | |
| 7,335,021 B2 | 2/2008 | Nikodem | |
| 7,419,375 B2 | 9/2008 | Farzin-Nia et al. | |
| 7,686,613 B2 | 3/2010 | Pospisil et al. | |
| 7,695,277 B1 | 4/2010 | Stevens | |
| 7,771,640 B2 | 8/2010 | Cosse | |
| 7,819,660 B2 | 10/2010 | Cosse | |
| 2002/0110777 A1 | 8/2002 | Abels et al. | |
| 2004/0131989 A1 | 7/2004 | Dellinger | |
| 2005/0255422 A1 * | 11/2005 | Cordato | 433/10 |
| 2006/0014116 A1 | 1/2006 | Maijer et al. | |
| 2006/0269891 A1 | 11/2006 | Miqui | |
| 2007/0042314 A1 | 2/2007 | Brosius | |
| 2008/0241782 A1 | 10/2008 | Abels et al. | |
| 2009/0325120 A1 | 12/2009 | Lewis et al. | |
| 2010/0092906 A1 | 4/2010 | Sabilla et al. | |
| 2010/0151403 A1 | 6/2010 | Tuneberg et al. | |
| 2010/0178628 A1 | 7/2010 | Kim | |
| 2010/0203463 A1 | 8/2010 | Huff et al. | |

* cited by examiner

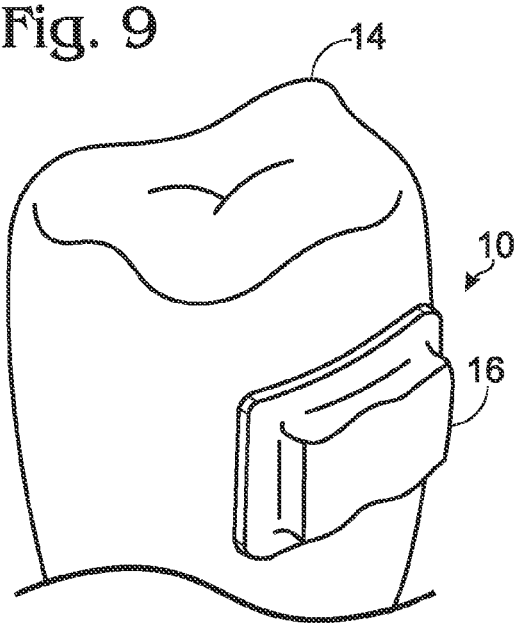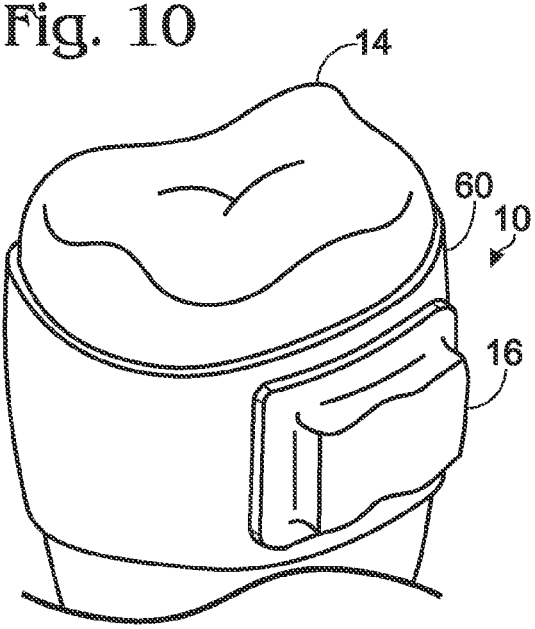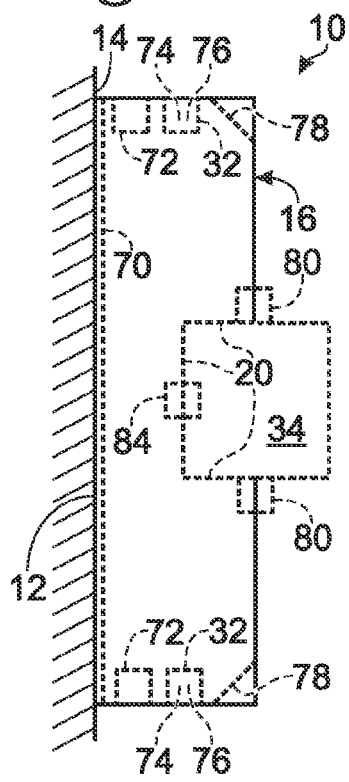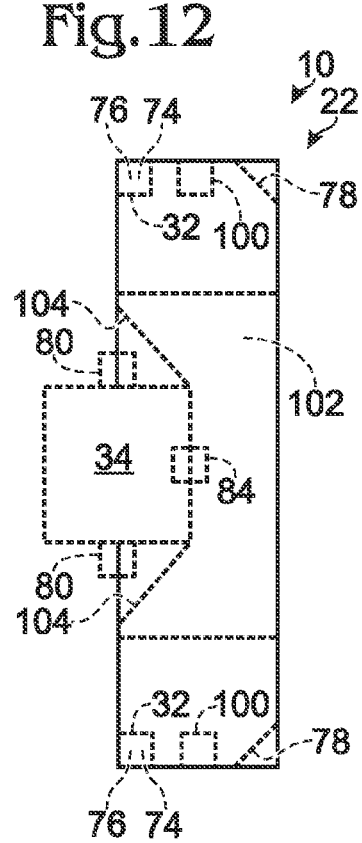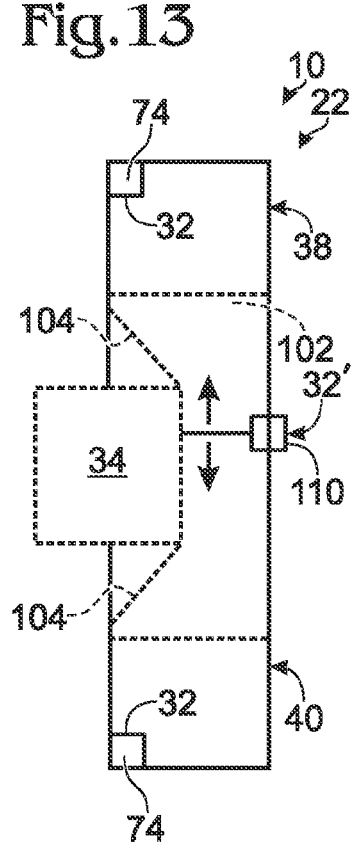

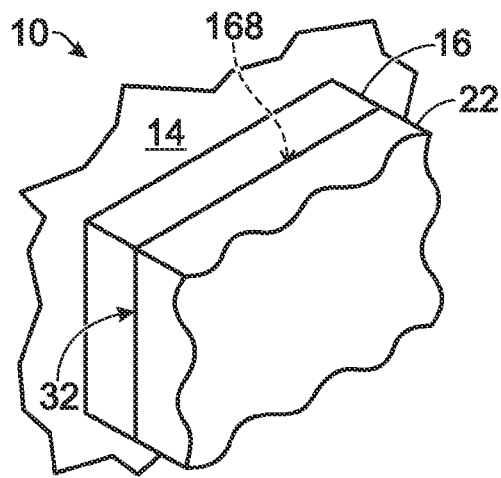
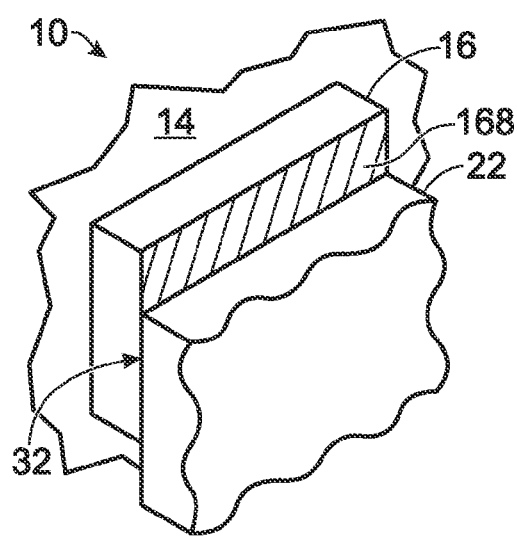
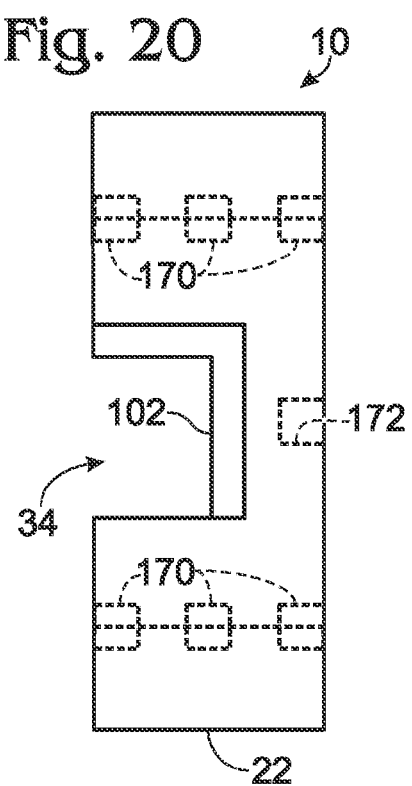
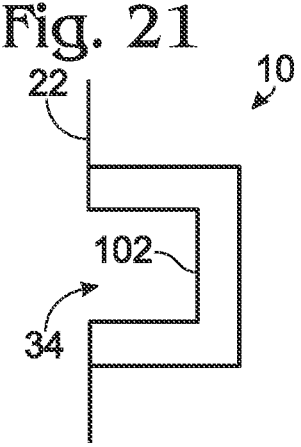
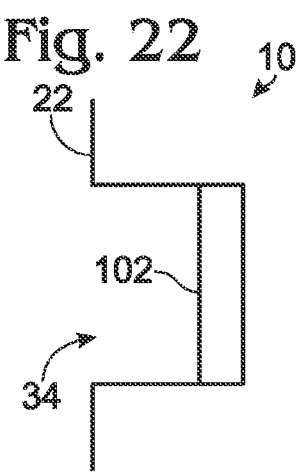

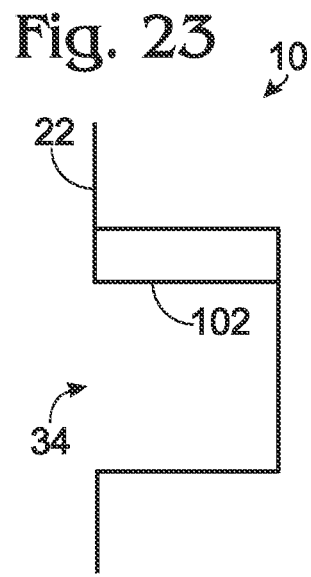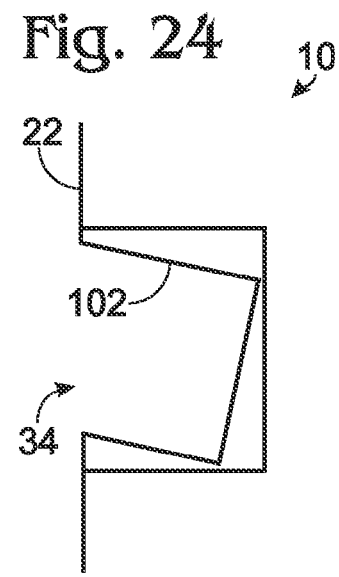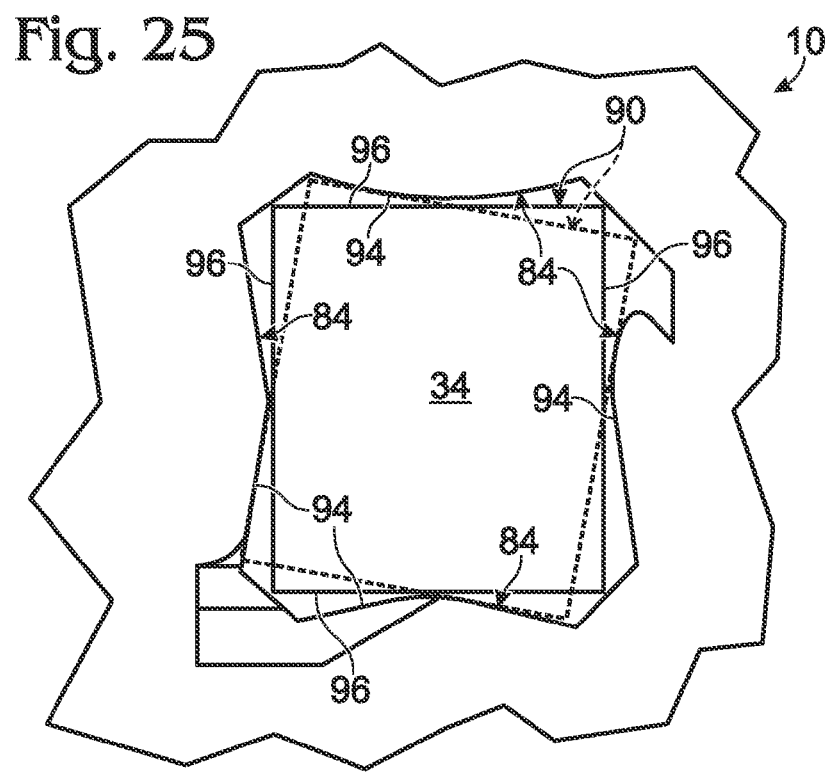

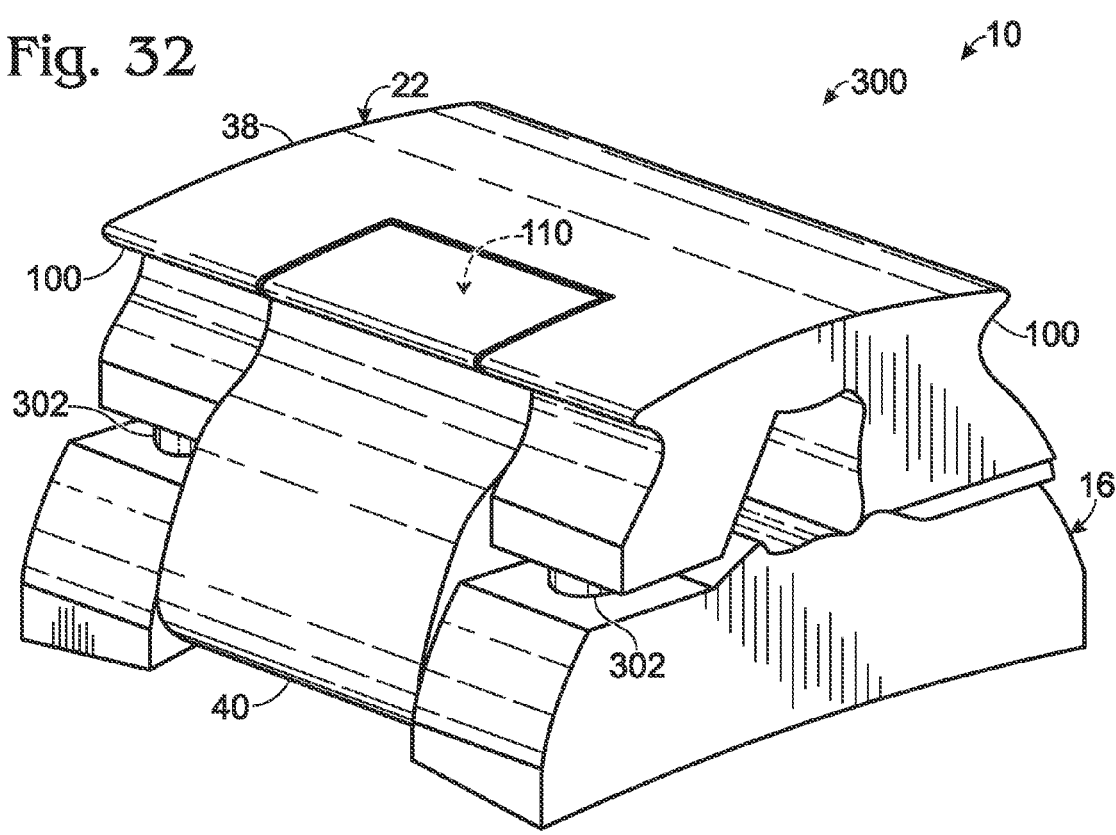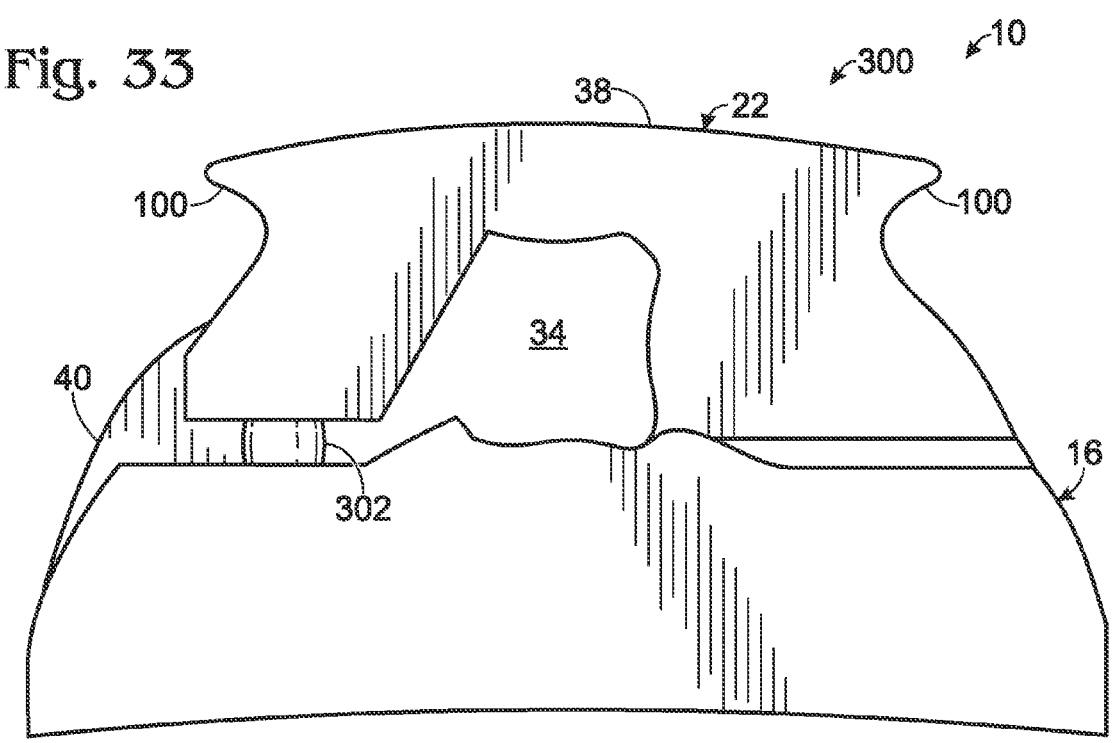

ORTHODONTIC APPLIANCE SYSTEMS

RELATED APPLICATIONS

The present application claims priority under 35 U.S.C. §119(e) to U.S. Provisional Patent Application Ser. No. 61/297,870, which is entitled "SELF-LIGATING ORTHODONTIC BRACKETS," which was filed on Jan. 25, 2010, and the disclosure of which is hereby incorporated by reference, and to U.S. Provisional Patent Application Ser. No. 61/434,946, which is entitled "SELF-LIGATING ORTHODONTIC BRACKETS," which was filed on Jan. 21, 2011, and the disclosure of which is hereby incorporated by reference.

FIELD OF THE DISCLOSURE

The present disclosure relates generally to orthodontic hardware and more particularly to orthodontic appliance systems.

BACKGROUND OF THE DISCLOSURE

Orthodontic brackets are typically small, slotted devices for use during orthodontic treatment. The brackets are usually configured for attachment to the front surfaces of teeth, either by directly cementing the bracket to a tooth surface or by bonding the bracket to a metal band that encircles the tooth, though they also may be attached to the back surfaces of teeth. The slots in the brackets, which may be referred to as archwire slots or archwire passages, are disposed horizontally or generally horizontally and are configured to receive an archwire. Traditionally, an archwire is a resilient, curved piece of wire that may be bent or twisted prior to installation in the bracket slots, with an archwire typically extending through the slots of all of the orthodontic brackets that are attached to a patient's upper or lower teeth. The engagement between the archwire and the brackets create corrective, or prescriptive, forces that are directed to the teeth by the orthodontic brackets to urge the teeth into a correct or desired alignment or occlusion.

The archwire may be secured in the bracket slots by a variety of mechanisms, such as depending on the bracket configuration. For example, a "ligating" bracket typically requires a separate fastener, such as a ligature wire or elastic band, which is tied or otherwise positioned around ligating structures, such as tie wings, on the bracket body to secure the archwire in place. A "self-ligating" bracket, on the other hand, typically includes a clamp, gate, or other self-locking mechanism, such as a closeable bracket slot, that allows such a bracket to retain the archwire without requiring the use of ligatures or other separate fasteners.

Expressed in slightly different terms, a conventional ligating bracket defines an archwire slot with an opening (typically extending in a plane generally parallel to the base of the bracket and/or surface of the corresponding tooth to which the bracket is secured) into which the archwire may be inserted into the slot (other than by axially inserting the archwire through the opposed ends of the archwire slot), with the opening requiring a ligature or other structure that is not part of the bracket to obstruct or otherwise close the opening to prevent removal of the archwire therethrough. In contrast, a conventional self-ligating bracket defines an archwire slot (such as may be similar or identical to the above-discussed archwire slot of a conventional bracket), but also includes a movable gate or closure. The gate, or closure, is coupled to the body of the bracket and is configured to be slid, pivoted, or otherwise moved from an open position, in which an archwire may be inserted into the archwire passage through the opening, to a closed position, in which the opening of the archwire passage is closed or otherwise obstructed to prevent removal of the archwire therethrough.

Illustrative, non-exclusive examples of ligating orthodontic brackets are disclosed in U.S. Pat. Nos. 6,302,688, 6,582,226, 4,597,739, 4,878,840, 3,772,787, 4,248,588, 4,492,573, 4,614,497, 4,698,017, 1,280,628, 1,821,171, and 3,435,527, the complete disclosures of which are hereby incorporated by reference. Illustrative, non-exclusive examples of self-ligating orthodontic brackets are disclosed in U.S. Pat. Nos. 6,659,766, 6,655,957, 6,358,045, 6,193,508, 5,857,850, 5,711,666, 5,562,444, 5,322,435, 5,094,614, 4,559,012, 4,531,911, 4,492,573, 4,419,078, 4,371,337, 4,077,126, 4,144,642, 4,248,588, 4,698,017, 3,772,787, 4,559,012, 4,561,844, 4,655,708, 4,077,126, 4,419,078, 4,197,642, 4,712,999, and 4,171,568, the complete disclosures of which are hereby incorporated by reference. Still further additional examples of orthodontic brackets are disclosed in U.S. Pat. Nos. 7,819,660, 7,771,640, and 6,632,088, the complete disclosures of which are hereby incorporated by reference. The structures, features, applications, and methods of the above-identified references may be utilized with and/or incorporated into orthodontic appliance systems according to the present disclosure to the extent that doing so does not conflict with the express provisions of the instant disclosure.

SUMMARY OF THE DISCLOSURE

Various orthodontic appliances and appliance systems are disclosed herein.

Some orthodontic appliance systems according to the present disclosure include an orthodontic bracket or bracket assembly, which may be a self-ligating bracket or bracket assembly, and a prescriptive, or prescription-altering, insert that is adapted to be removably coupled to the bracket. In some embodiments, the prescriptive insert may be optional, in that the bracket may alone define a unique orthodontic prescription. In some embodiments, the prescriptive insert may define and/or alter the prescription of the bracket. Additionally, a plurality of prescriptive inserts may be provided, with each insert defining a unique orthodontic prescription with the bracket when the insert is coupled to the bracket.

Some orthodontic appliance systems according to the present disclosure include a self-ligating bracket assembly and include a base and a closure coupled to the base, and in some embodiments removably coupled to the base. In some embodiments, a plurality of closures may be provided, with each closure defining a unique orthodontic prescription with the base when the closure is coupled to the base.

Also disclosed herein are bracket assemblies, including self-ligating bracket assemblies, that are configured to redirect and/or absorb mechanical forces that are applied to the bracket assembly without debonding from the tooth or being damaged. The bracket assembly may be designed to absorb these forces through the inclusion of one or more of a variety of features, including force-directing or force-deflecting structures on the outer surface of the bracket assembly; connecting assemblies between the base and the cap that may include shock-absorbing capabilities and/or may be displaced a certain distance from their equilibrium position without damage; floating hinges that interconnect a closure portion of the self-ligating bracket assembly with a base portion of the self-ligating bracket assembly; and/or connecting assemblies that are designed to release, or disengage, the cap from the base, thus releasing the arch wire, prior to the bracket assembly being damaged or debonded from the tooth.

Further disclosed are bracket assemblies that are configured to define a plurality of archwire passages that permit more than one defined, or predefined, orientation of an associated archwire. Other configurations of orthodontic appliance systems and bracket assemblies also are disclosed herein.

BRIEF DESCRIPTION OF THE DRAWINGS

FIG. 9 is an isometric schematic view of a portion of an illustrative bracket assembly according to the present disclosure bonded to a tooth surface.

FIG. 10 is an isometric schematic view of a portion of an illustrative bracket assembly according to the present disclosure bonded to a tooth-surrounding band structure, which in turn is coupled to a tooth.

FIG. 11 is a schematic view of an illustrative, non-exclusive example of a base portion of a bracket assembly according to the present disclosure, with the base portion shown bonded to a tooth surface, and further illustrating several optional base features.

FIG. 12 is a schematic view of an illustrative, non-exclusive example of a one-piece closure portion of a bracket assembly according to the present disclosure, showing several optional closure features.

FIG. 13 is a schematic view of an illustrative, non-exclusive example of a two-piece closure portion of a bracket assembly according to the present disclosure, showing several optional closure features.

FIG. 18 is a schematic, fragmentary isometric view of a portion of a bracket assembly according to the present disclosure, with the bracket assembly shown attached to a tooth with the base and closure correctly aligned with each other such that alignment indicia cannot be seen.

FIG. 19 is a schematic, fragmentary isometric view of a portion of a bracket assembly according to the present disclosure, with the bracket assembly shown attached to a tooth with the base and closure misaligned such that alignment indicia can be seen.

FIG. 20 is a schematic view of an illustrative, non-exclusive example of a closure portion of a bracket assembly according to the present disclosure together with an illustrative, non-exclusive example of a prescriptive insert according to the present disclosure.

FIG. 21 is a fragmentary schematic view of a closure portion of a bracket assembly according to the present disclosure together with an illustrative, non-exclusive example of a prescriptive insert according to the present disclosure.

FIG. 22 is a fragmentary schematic view of a closure portion of a bracket assembly according to the present disclosure together with an illustrative, non-exclusive example of a prescriptive insert according to the present disclosure.

FIG. 23 is a fragmentary schematic view of a closure portion of a bracket assembly according to the present disclosure together with an illustrative, non-exclusive example of a prescriptive insert according to the present disclosure.

FIG. 24 is a fragmentary schematic view of a closure portion of a bracket assembly according to the present disclosure together with an illustrative, non-exclusive example of a prescriptive insert according to the present disclosure.

FIG. 25 is a fragmentary schematic view of an illustrative, non-exclusive example of a bracket assembly according to the present disclosure, illustrating more than one orientation of an associated archwire within the archwire passage.

FIG. 32 is an assembled isometric view of another illustrative, non-exclusive example of a bracket assembly according to the present disclosure.

FIG. 33 is an assembled side elevation view of the bracket assembly of FIG. 32, with the bracket assembly illustrated in a closed configuration.

DETAILED DESCRIPTION AND BEST MODE OF THE DISCLOSURE

Figure 1:
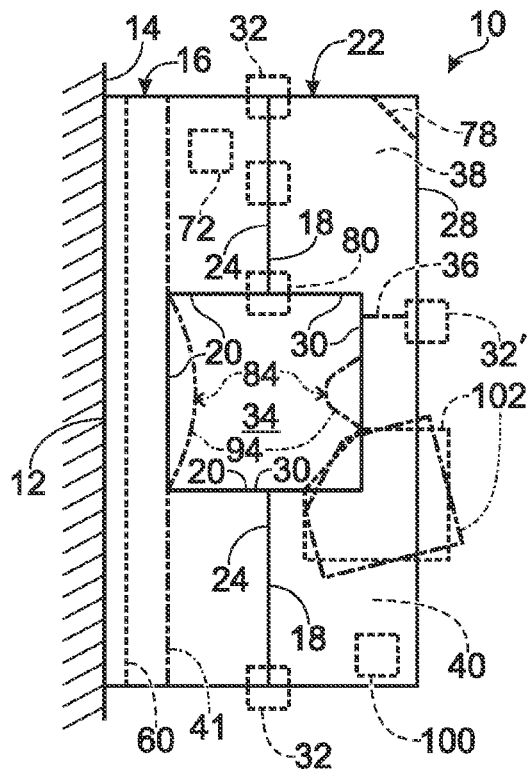
FIG. 1 is a schematic illustration representing illustrative, non-exclusive examples of orthodontic appliances and orthodontic appliance systems according to the present disclosure.

Various illustrative embodiments of orthodontic appliances 10, which also may be referred to herein as bracket assemblies, are presented herein. As schematically represented in FIG. 1, bracket assemblies 10 according to the present disclosure include a base 16 that may be bonded or otherwise directly or indirectly secured to a tooth 14. When a bracket assembly 10 is a self-ligating bracket assembly, it typically and additionally includes a closure, or cap, 22 that is operatively and releasably attached or otherwise coupled to the base. When including both a base and a closure, the collective assembly may be described as a self-ligating bracket assembly, or just as a bracket or bracket assembly. Additionally or alternatively, orthodontic appliances according to the present disclosure may not include a closure that is separate and apart from a base, and such appliances also may be referred to as bracket assemblies or simply as brackets.

As discussed herein and as schematically illustrated in FIG. 1, bracket assemblies 10 according to the present disclosure additionally may include one or more of such illustrative, non-exclusive features, structures, portions, components, variations, characteristics, etc. as (and/or may be configured to be utilized with one or more of) connecting assemblies 32, a tooth surrounding band 60, base ligating structure 72, closure ligating structure 100, force-deflecting structure 78, archwire retaining structure 80, archwire locating structure 84, and/or prescriptive inserts 102. These and other optional features are discussed in detail herein with respect to the various schematic and other illustrations presented. While each of these various optional features may not be discussed in detail with respect to FIG. 1, FIG. 1 schematically illustrates that each of these various optional features, structures, portions, components, variations, characteristics, etc., may be included in a bracket assembly 10 according to the present disclosure, and the subsequently discussed individual figures do not limit embodiments of bracket assemblies to the illustrated versions depicted therein.

Base 16 may be attached to tooth 14 (or optionally a band that is secured around the tooth) via an attaching surface 12 and extends from the attaching surface to at least one base mating surface 18, which is configured to mate with one or more corresponding closure mating surfaces 24 of the closure 22, when present. Closure 22, when present, extends from closure mating surfaces 24 to an external surface 28, which typically will extend generally parallel to the surface of the tooth to which the bracket assembly is attached.

Together, base 16 and closure 22 (when present) of bracket assemblies 10 according to the present disclosure define an archwire passage 34, which is sized and positioned to receive an archwire and to direct resulting corrective forces to the tooth to which the bracket assembly is attached. Stated differently, a bracket or bracket assembly according to the present disclosure may include a plurality of bracket archwire contacting, or engaging, surfaces that are configured to engage an associated archwire when the archwire is received in the archwire passage. As used herein, the archwire that is inserted into an archwire passage of a bracket assembly 10 may be (but is not required to be) referred to as an "associated archwire" to indicate that it is interacting with the bracket assembly, such as by contacting one or more sides, or walls, of the archwire passage of the bracket assembly, and when in use, applying prescriptive forces to a patient's corresponding teeth.

As discussed in more detail herein, the corrective forces imparted to a tooth may be generated by the archwire exerting forces against the bracket assembly (such as against the portions of the closure and/or the base that define the archwire passage—i.e., the bracket archwire contacting surfaces and/or the insert archwire contacting surfaces, when present), by the bracket assembly against the archwire, or both. Archwire passage 34 may additionally or alternatively be referred to as an archwire hole, an archwire slot, and/or an archwire receiver. Also within the scope of the present disclosure are bracket assemblies or brackets that do not include a closure 22, and in which the base, or bracket as a whole, defines an archwire passage 34. Such brackets according to the present disclosure, which may be described as non-self-ligating brackets, may include any of the additional and suitable features of bracket assemblies discussed herein without requiring the inclusion of a closure 22.

Although not required to be, some bracket assemblies 10 according to the present disclosure are self-ligating bracket assemblies. Accordingly, in such embodiments, the bracket assemblies are designed and shaped so that the archwire is received and retained in the archwire passage without requiring the use of separate ligating bands or wires. Accordingly, when in use to apply corrective forces to a patient's tooth, bracket assemblies 10 define a closed boundary around an archwire that is properly inserted into the archwire passage. By "closed boundary," it is meant that the archwire passage defined by the bracket assembly bounds, or surrounds, an archwire (as considered from the perspective of a plane that is transverse to the longitudinal axis of the archwire and/or the archwire passage) that is received through the passage such that the archwire cannot be removed from the archwire passage other than by sliding the archwire in a longitudinal, or axial, direction, as measured relative to the archwire. In other words, the bracket assembly defines an opening (typically extending generally parallel to the base, or body, of the bracket assembly) into which an archwire may be inserted and removed from the archwire passage, with a self-ligating bracket assembly further including a closure to selectively obstruct this opening. When in use to apply corrective forces to a patient's tooth, self-ligating bracket assemblies 10 form an archwire passage that does not provide an opening of sufficient size for the archwire to be removed from the archwire passage by translating or otherwise moving the archwire in a lateral, or transverse, direction measured with respect to the archwire passage.

As schematically illustrated in FIG. 1, archwire passage 34 may be defined by surfaces of base 16 and closure 22, such as base slot surfaces 20 and closure slot surfaces 30. Specifically, archwire passage 34 may be defined collectively by at least one surface of base 16 and at least one surface of closure 22, and in some bracket assemblies according to the present disclosure, may be defined by at least two surfaces of base 16 and/or at least two surfaces of closure 22.

Self-ligating bracket assemblies according to the present disclosure may be selectively configured between an open, or installation, configuration and a closed, or corrective, configuration. A closed configuration refers to when the closure and base of an installed bracket assembly are operatively coupled together to receive and retain an archwire within the archwire passage, and thereby to transmit corrective forces to the patient's tooth. When the archwire is positioned within the archwire passage of a bracket assembly 10 that is in a closed configuration, the archwire is retained within the archwire slot, which as discussed, defines a closed boundary (measured transverse to the axis of the portion of the archwire received within the archwire passage and/or the transverse axis of the archwire passage) around the archwire. In this closed configuration, the archwire optionally also may be at least frictionally retained against longitudinal, or axial, movement relative to the archwire passage, but the bracket assembly does not provide a physical barrier against longitudinal movement of the archwire relative to the archwire passage. In contrast, in the open configuration, at least a portion of the closure is moved relative to the base to permit removal of the archwire from the archwire passage in a direction other than in an axial, or longitudinal direction (measured relative to the axis of the portion of the archwire that is received within the archwire passage), such as through an opening in the archwire passage that is not obstructed when the closure is moved to the open configuration. In other words, in the open configuration, an archwire may be inserted into and/or removed from the archwire passage, such as in a translational direction measured relative to the base of the bracket assembly, and/or by respectively moving the archwire toward or away from the tooth to which the base of the bracket assembly is secured. In the open configuration, the archwire passage of the bracket assembly does not define a closed boundary around the portion of an archwire received therein (as measured transverse to the longitudinal axis of the archwire and/or archwire passage), thereby providing an opening or slot through which the archwire may be inserted into and/or removed from the archwire passage.

Closure 22 is coupled, and in some embodiments removably coupled, to base 16 by at least one connecting assembly 32, which provides for at least one of pivotal, releasable, and/or separable coupling of the cap to the base. As used herein, a connecting assembly that is configured to provide releasable, or removable, coupling between the closure and the base refers to a connecting assembly that is designed, or constructed, to provide for repeated engagement and disengagement of the corresponding portions of the coupling assembly, the closure, and/or the base without destruction of the closure, the base, or the connecting assembly. As further used herein, this selective releasing of the closure from the base means that at least the portion of the closure that was coupled to the base by the connecting assembly may be selectively pivoted or otherwise moved away from the corresponding portion of the base, such as to configure the bracket assembly from its closed configuration to its open configuration and thereby permit the insertion of an archwire into the archwire passage or the removal of an archwire from the archwire passage. In some embodiments, the one or more connecting assemblies may provide for partial and/or complete separation of the closure from the base, with partial separation referring to a portion of the closure pivoting or otherwise moving away from the base while another portion of the closure remains connected to the base. In contrast, complete separation of the closure from the base refers to the entirety of the closure being removed, and thus being spaced apart and/or disconnected, from the base.

A connecting assembly 32 may additionally or alternatively be referred to as a coupling assembly and/or a coupler, and may include any suitable structure that provides for the selective coupling of the closure and the base. In at least FIG. 1, connecting assemblies 32 are depicted as dashed boxes to schematically represent that the shape, size, and number of components of connecting assemblies may vary without departing from the scope of the present disclosure. A connecting assembly may include a portion that is attached to, permanently attached to, or even integrally formed with at least a portion of the closure and/or the base, and the connecting assembly may include any suitable number of components, or portions, to provide for the selective coupling of the base and the closure. When the bracket assembly is in the open configuration, a connecting assembly may (but is not required in all embodiments to) include a portion that is connected to the closure and a separate portion that is connected to the base, with these portions being interconnected when the bracket assembly is reconfigured to its closed configuration. Connecting assemblies 32 may be configured to allow closure 22 to release from base 16 responsive to an external force that is applied to orthodontic appliance 10 and without damaging or destroying the connecting assembly, the closure, or the base. Connecting assembly 32 may include one or more of a hinge, clasp, and/or other fastening structures and optionally may further include resilient structures placed between base 16 and closure 22 to dampen external forces applied to the bracket assembly and/or to lock the closure and/or fastening structures in a closed configuration.

Figure 2:
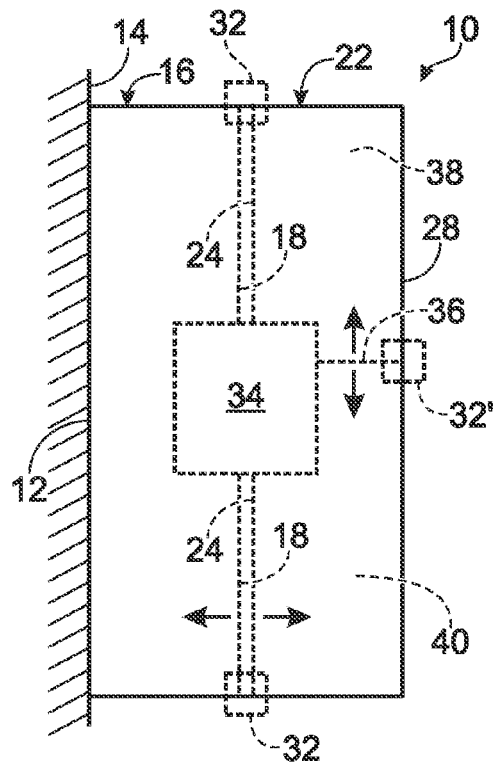
FIG. 2 is a schematic view of an illustrative, non-exclusive example of a self-ligating orthodontic bracket assembly according to the present disclosure, with the bracket assembly including a base portion and a closure portion.

Self-ligating orthodontic appliances 10 according to the present disclosure may be described herein as being "multi-piece" orthodontic appliances. As used herein, "multi-piece" refers to an orthodontic appliance that is a composite structure consisting of at least two components, namely, at least a base 16 and a closure 22. Therefore, orthodontic appliances according to the present disclosure may include two components, three components, four components, or more. The base and the closure may be single-piece components, such as which include a monolithic body. However, it is also within the scope of the present disclosure that the base and the closure themselves may be composite structures consisting of two or more separable subcomponents, or that the various components and structural features of each assembly may be integrally formed. Accordingly, base 16 and closure 22 may include two or more interconnected components, or may be formed as a single piece, or component. Regardless of the number of components, it is within the scope of the present disclosure that base 16 and closure 22 may additionally or alternatively be respectively referred to herein as a base assembly 16 and a closure assembly 22. As discussed herein, closure 22 may be of single-piece construction or may be made of multiple pieces. An optional closure division, or divisions, 36 may divide the closure into multiple pieces, including two pieces, three pieces, or more than three pieces. As schematically shown by arrows in FIG. 2, the specific location, shape, and/or orientation of closure division 36 may vary. When closure 22 is divided into two or more pieces, or components, by a closure division, the closure may include at least one closure connecting assembly 32' that selectively (and releasably) interconnects and retains together the portions of the closure. Closure connecting assembly 32' may include any of the structure, features, and/or variants described and/or illustrated herein with respect to connecting assemblies 32, which optionally may be referred to as closure-to-base connecting assemblies 32. Base mating surfaces 18 and closure mating surfaces 24 are schematically illustrated in FIG. 2 in dashed lines and with accompanying arrows to indicate that their locations, shapes, and/or orientations also may vary without departing from the scope of the present disclosure. Archwire passage 34 also is shown in dashed lines in FIG. 2 to schematically indicate that its specific shape, location, and the proportion of the archwire passage formed by the base and cap, respectively, may vary. Thus, archwire passage 34 may have one or more surfaces formed by base 16 and one or more surfaces formed by closure 22, archwire passage 34 may be closer to or farther from the tooth than the relative distances shown, and base 16 and closure 22 may be constructed of one or more pieces and vary in relative size and/or shape without departing from the scope of the present disclosure.

Figure 3:
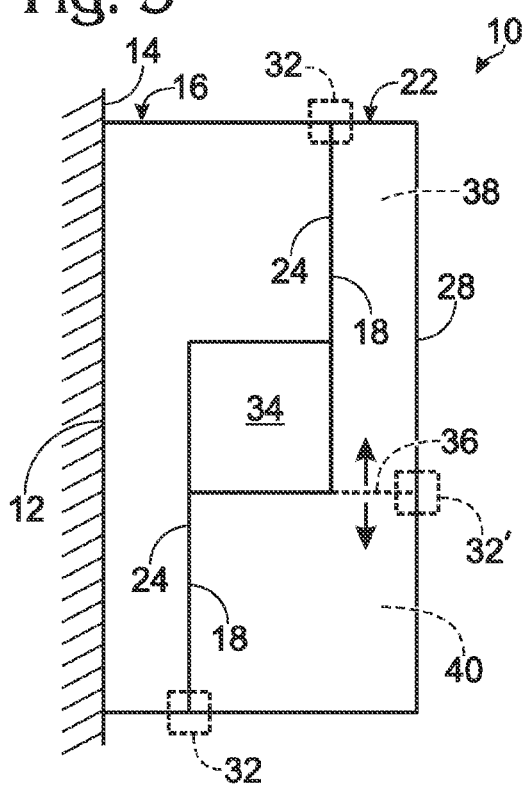
FIG. 3 is a schematic view of another illustrative self-ligating orthodontic bracket assembly according to the present disclosure.
Figure 4:
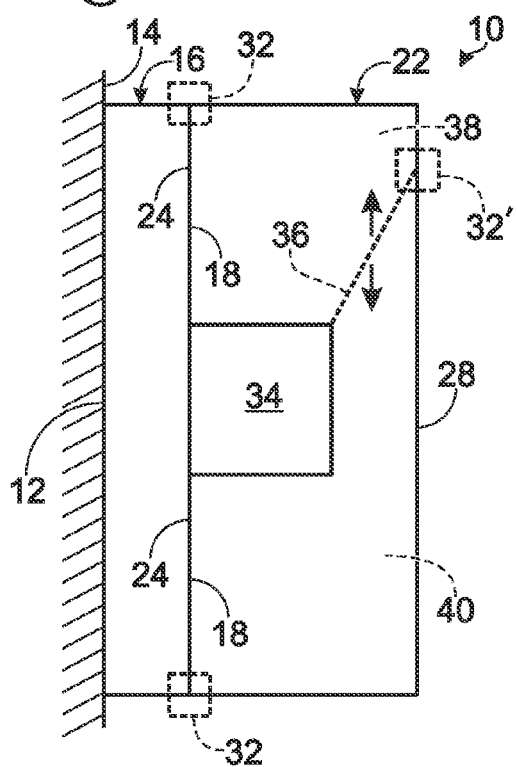
FIG. 4 is a schematic view of another illustrative self-ligating orthodontic bracket assembly according to the present disclosure.
Figure 5:
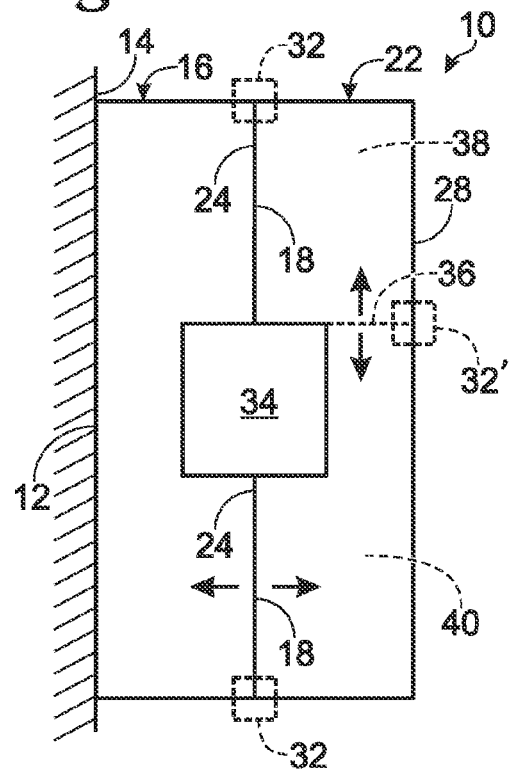
FIG. 5 is a schematic view of another illustrative self-ligating orthodontic bracket assembly according to the present disclosure.
Figure 6:
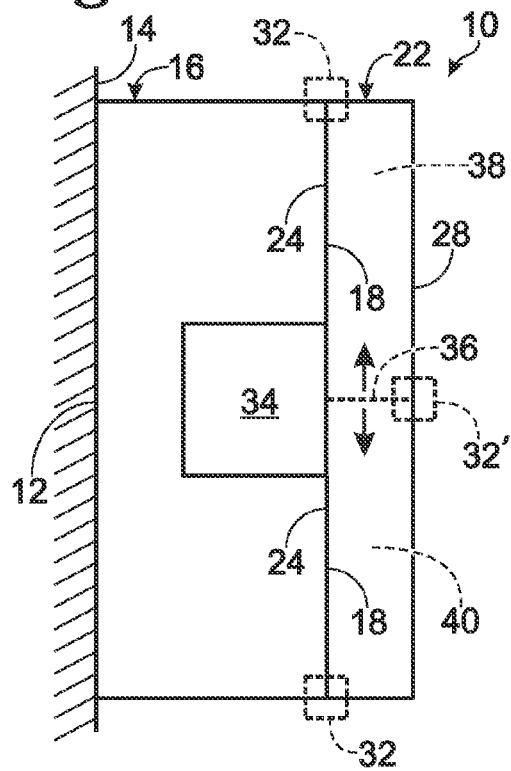
FIG. 6 is a schematic view of another illustrative self-ligating orthodontic bracket assembly according to the present disclosure.

FIGS. 3-6 provide schematic, illustrative, non-exclusive examples of other suitable base and closure embodiments according to the present disclosure. In all of these embodiments, closure division 36 is schematically indicated to be optional and its location and orientation are varied to illustrate that it may or may not be present and that it may take on any suitable shape or be in any suitable location. In FIG. 3, base 16 defines two complete surfaces or sides of archwire passage 34, and closure 22 defines two additional surfaces or sides of archwire passage 34. Optional closure division 36 may define first or upper closure portion 38 and second or lower closure portion 40 and may be generally coplanar with the bottom surface of archwire passage 34. In FIG. 4, base 16 defines one complete surface or side of archwire passage 34, and closure 22 defines three additional surfaces or sides of archwire passage 34. This optional configuration is also schematically illustrated in FIG. 1, with the dash-dot line at 41. The optional closure division 36 of the schematic illustration of FIG. 4 is at an inclined angle relative to the archwire passage surfaces. In FIG. 5, base 16 and closure 22 both define one complete surface and two partial surfaces or sides of archwire passage 34. Optional closure division 36 is coplanar with the top surface or side of archwire passage 34; however, this coplanar configuration is not required. In FIG. 6, base 16 defines three complete surfaces or sides of archwire passage 34, and closure 22 defines an additional surface or side of archwire passage 34. Optional closure division 36 is parallel to but not coplanar with the upper surface or side of archwire passage 34.

Figure 7:
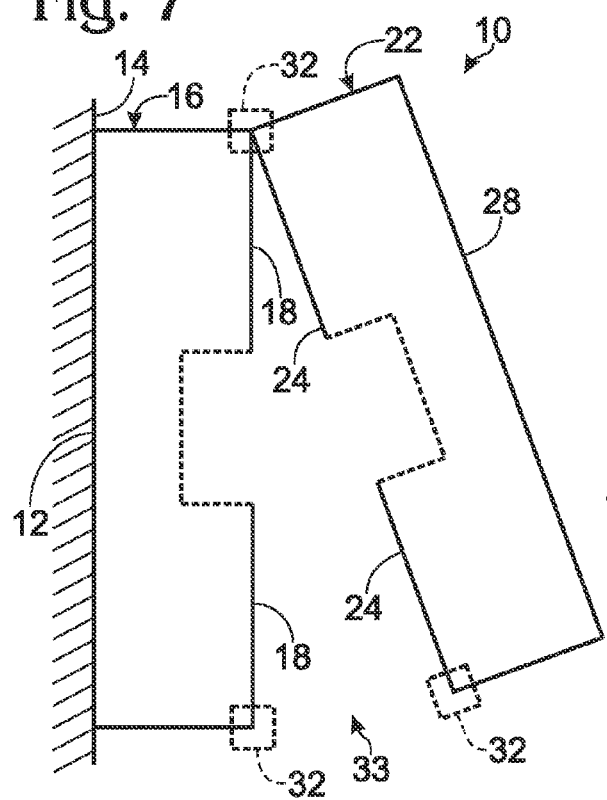
FIG. 7 is a schematic view of an illustrative self-ligating orthodontic bracket assembly according to the present disclosure, with a one-piece closure portion and with the assembly shown in an open configuration.
Figure 8:
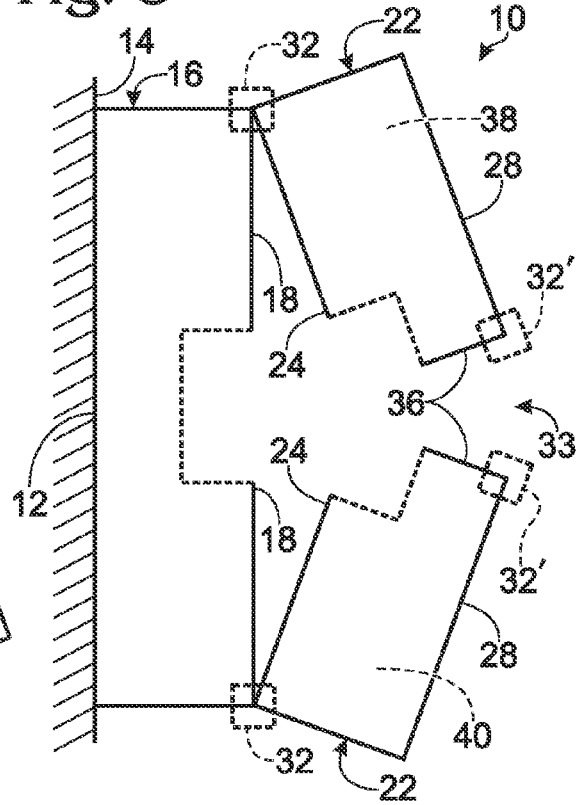
FIG. 8 is a schematic view of an illustrative self-ligating orthodontic bracket assembly according to the present disclosure, with a two-piece closure portion and with the assembly shown in an open configuration.

In FIGS. 1-6, self-ligating bracket assembly 10 has been shown in a closed configuration, in which base mating surfaces 18 and closure mating surfaces 24 are proximate each other to define the previously discussed "closed boundary" for retaining an archwire in the bracket assembly's archwire passage. As discussed, bracket assembly 10 also may be configured to an open configuration, in which the archwire passage includes an opening 33 through which an archwire may be selectively inserted into and removed from the archwire passage (other than by sliding the archwire axially along the longitudinal axis of the archwire passage). Illustrative, non-exclusive examples of self-ligating bracket assemblies 10 in an open configuration are schematically illustrated in FIGS. 7 and 8. FIG. 7 illustrates an open configuration for an illustrative, non-exclusive example of a bracket assembly 10 that includes a one-piece closure 22. In FIG. 7, closure 22 hinges from (i.e., is pivotally coupled to) base 16 by connecting assembly 32. FIG. 8 illustrates an example of an open configuration for an illustrative, non-exclusive example of a bracket assembly 10 that includes a two-piece closure 22, with the closure comprising first (upper) closure portion 38 and second (lower) closure portion 40. In this embodiment, both first closure portion 38 and second closure portion 40 hinge from (i.e., are pivotally coupled to) base 16 by connecting assemblies 32. It is also within the scope of the present disclosure that closure 22 is not attached to base 16 by a connecting assembly 32 in the form of a hinge. As illustrative, non-exclusive examples, closure 22 may snap onto base 16, be configured to slide relative to base 16 via slots, or be attached by any other suitable structure or releasable fastening or coupling mechanism.

While archwire passage 34 is schematically illustrated as being rectangular in FIGS. 1-8, it is within the scope of the present disclosure that archwire passage 34 may have any desired cross-sectional shape, including rectangular, square, circular, semi-circular, elliptical, triangular, trapezoidal, any polygonal or non-polygonal shape, irregular, symmetrical, monolithic, braided, uniform, and/or non-uniform, may not have a constant cross-section, or profile, and may contain internal structures that cause it to depart from an idealized geometry. It is also within the scope of the present disclosure that the archwire passage may not form a continuous perimeter around the cross-section of the archwire but simply may serve, or function, to retain the archwire within a desired location. Thus, the archwire passage may comprise a hook, clip, or other structure that constrains the archwire within a defined region. The location of archwire passage 34 also may vary from the locations shown, with varying portions being formed by base 16 and closure 22. It is also within the scope of the present disclosure that either base 16 or closure 22 forms all surfaces or sides of archwire passage 34. Base 16 and closure 22 may contain additional structures and/or features not shown in the preceding figures and may not comprise regular geometric shapes, as discussed herein.

In FIGS. 1-8, closure division 36 has been schematically illustrated as a planar structure that serves to divide closure 22 into upper 38 and lower 40 (as viewed in the schematic illustration) closure portions. While FIGS. 1-8 show that the closure division can have any location and/or orientation, it is also within the scope of the present disclosure that closure division 36 is not planar and may take on any desired shape. In addition, closure 22 may include a plurality of cap divisions, and thus may include a plurality of closure portions. While these closure portions may form the archwire passage via simple planar contact among the various closure portions, it is also within the scope of the present disclosure that the contact between closure portions be more complicated, including arcuate contact regions and/or interleaved closure portions. Similarly, the base mating and closure mating surfaces discussed herein may have any suitable shape, including planar and non-planar geometries. In addition, it is within the scope of the present disclosure that any structures associated with bracket assembly 10 such as, for example, connecting assembly 32, may be integrally formed as a monolithic part of the closure and/or base. It is also within the scope of the present disclosure that these structures be separately formed of the same or different materials and operatively attached to the various components of the bracket assembly.

In FIGS. 1-8, base 16 has been schematically illustrated as being attached directly to tooth 14 via attaching surface 12. This is shown somewhat schematically in FIG. 9, where base 16 is operatively attached directly to the tooth surface using a suitable bonding media, such as cement and/or other adhesive. As shown in FIG. 10, it is also within the scope of the present disclosure that base 16 be operatively attached to a tooth-surrounding band 60, with tooth-surrounding band 60 encircling the tooth and securing the band-base assembly firmly on the tooth. Base 16 may be attached to band 60 using any suitable method, such as bonding using cement and/or adhesive, welding, brazing, soldering, or other known bonding techniques.

Illustrative, non-exclusive examples of additional structures and features that optionally may be included on base 16 of a bracket assembly 10 according to the present disclosure are schematically shown in FIG. 11. In FIG. 11, base 16 is operatively attached to tooth 14 via attaching surface 12, which may include an adhesion promotion structure 70. Adhesion promotion structure 70 may include any structure that increases the strength of the bond between tooth 14 and attaching surface 12, including structures that increase the adhesive strength, such as surface coatings, treatments, and/or modifications, structures that increase the surface area for bonding, such as regular or irregular surface roughening and/or patterning, and/or structures that increase the mechanical interaction between the adhesive and the attaching surface, such as three-dimensional meshes, grids, or screens that allow the adhesive to physically interlock with the attaching surface.

Base 16 also may include one or more base ligating structures 72, which may include channels, grooves, tie wings, or other structures that are sized, shaped, and/or positioned to receive and retain a ligature and/or an orthodontic chain or powerchain. As used herein, a ligating structure is a structure that is designed or configured to accept and retain a ligature; a ligature is any suitable material, such as a wire, elastic band, or resilient material, that is accepted within a ligating structure and serves to retain an object, such as an archwire, closure 22, or even another bracket assembly, in a defined region relative to the object containing the ligating structure; and an orthodontic chain is a resilient material, such as a chain of resilient bands, that is attached to two or more bracket assemblies and may serve to retain an archwire on the bracket and/or apply a force that serves to urge two or more teeth closer together. Base ligating structure 72 may be used in conjunction with a ligature to more firmly secure the archwire in a defined position relative to the bracket assembly, or portion thereof, allowing base 16 to function as a traditional, ligating orthodontic bracket assembly. Base ligating structure 72 may be used to secure a closure of a bracket assembly into a fixed orientation relative to the base, such as in an orientation from which the closure is not released until the corresponding ligature is removed. When present and in use, this may reduce or eliminate the shock-absorbing and self-ligating features of brackets according to the present disclosure but may, in certain circumstances, allow an orthodontist to apply a greater force to a tooth than can be applied with bracket assemblies according to the present disclosure. The base ligating structure also may be used in conjunction with an orthodontic chain to chain, or link, multiple teeth together and move them toward each other.

Base 16 may further include one or more connecting assemblies 32, such as hinge 74 or clasp 76 structures, or portions thereof. Hinge 74 and clasp 76 structures according to the present disclosure serve to operatively attach base 16 to a closure and/or to attach separate pieces of a multi-piece base or closure together and are discussed in more detail herein. As also shown in FIG. 11, base 16 of a bracket assembly 10 according to the present disclosure may include other optional structures, such as force-deflecting (or force-directing) structures 78, archwire retaining structures 80, and archwire locating structures 84.

Force-deflecting structures 78 according to the present disclosure are designed to modify external forces applied to base 16 in order to minimize the potential for base 16 to be debonded from tooth 14 or be damaged by the external force. For example, occlusal forces associated with chewing or otherwise biting upon a hard object may be quite large. Thus, if a patient inadvertently allows a hard object, such as a fork, to contact an edge of base 16 while chewing, the resultant shear force may be sufficient to debond or otherwise damage base 16. Force-deflecting structures 78 may include angled surfaces, which may be located on edge portions of the base, that effectively convert these shear forces into peel forces, minimizing the potential for debonding or damage to the base. By "angled," it is meant that these surfaces extend at an inclined, or oblique, angle relative to the tooth's surface to which the bracket assembly is attached.

Archwire retaining structures 80 are structures that may serve to constrain or otherwise locate the edges of the archwire within a defined region, such as base slot surface 20. Additionally or alternatively, referring back to FIG. 1, archwire locating structures 84 may include a convex projection, or surface, 94, which may serve to locate a flat surface of an archwire. Convex projection 94 is an illustrative, non-exclusive example of archwire locating structure 84. Other shapes may be used, the number of structures may vary, the structures may be present on any number of base and/or closure surfaces, and/or the location of the structures may be changed without departing from the scope of the present disclosure.

Illustrative, non-exclusive examples of additional structures that may be included on closure 22 of a bracket assembly 10 according to the present disclosure are schematically shown in FIG. 12. Closure 22 may include at least one or even several structures that are similar and/or complementary to structures on a base, including connecting assemblies 32 (or a portion thereof), which may comprise a hinge 74 and/or a clasp 76, closure ligating structure 100, force-deflecting structure 78, archwire retaining structure 80, and archwire locating structure 84.

In addition, closure 22 also may include and/or may be configured to receive an optional insert, or prescriptive insert, 102, which may be selectively inserted into closure 22 and will be discussed in more detail herein. Prescriptive insert 102 additionally or alternatively may be referred to as a prescription-altering insert in that it is configured to change the prescription, or forces that are applied to a patient's tooth when a bracket assembly 10 with the insert is used, as compared to when the bracket assembly is used without the insert and/or with a different (i.e., differently sized, shaped and/or positioned) insert. Closure 22 also may include closure attachment clearance structures 104, which serve to provide clearance between closure 22 and an associated archwire, such that if closure 22 is attached to base 16 using a hinge, such as shown in FIGS. 7 and 8, the bracket assembly may be moved from the open configuration to the closed configuration without the closure contacting and/or displacing the archwire prior to reaching the closed configuration. This may minimize the forces that are placed on a tooth by the archwire when the bracket assembly is assembled and may increase patient comfort.

Similar to the discussion above with respect to base ligating structure 72, closure ligating structure 100 may serve a variety of purposes. As an illustrative, non-exclusive example, the closure ligating structure may be used in combination with a ligature to lock or otherwise secure the closure in a defined position relative to the base. This may decrease the likelihood that the closure will separate from the base and may allow an orthodontist to apply greater corrective forces to a tooth. In addition, closure ligating structure 100 also may be used in conjunction with an orthodontic chain or power chain to apply forces that may serve to move individual teeth closer together. Since, when used in conjunction with closure ligating structure 100, the orthodontic chain may not contact the archwire, low frictional forces between the archwire and the bracket assembly may be maintained.

As discussed herein, both base 16 and closure 22 may comprise one piece or a plurality of pieces. An illustrative, non-exclusive example of a closure 22, which comprises a first closure portion 38 and a second closure portion 40, is shown in FIG. 13. In FIG. 13, closure 22 schematically includes connecting assemblies 32 that comprises two hinge assemblies 74 (or portions thereof), which operatively connect the first and second closure portions to a corresponding base 16. In addition, a closure connecting assembly 32', in the form of a fastening structure 110, serves to connect the first and second closure portions to each other at least when the closure is in the closed configuration.

The forces acting on bracket assembly 10, base 16, closure 22, and/or an associated archwire may be corrective, or prescriptive, in nature, referring to a force administered in the course of orthodontic treatment, or external and non-corrective, referring to forces applied outside of, or not for, orthodontic treatment. Illustrative, non-exclusive examples of external, or non-corrective, forces include, but are not limited to, forces that are applied during such daily activities as chewing food, brushing teeth, or biting upon a hard object. Such forces are usually applied in a gingival direction, from an occlusal direction, or otherwise generally parallel to the plane of the tooth surface. When such forces encounter an orthodontic bracket of monolithic body construction, such as a conventional ligating or self-ligating bracket, the bracket is usually urged to one side, effectively shearing the bracket from its position on a tooth. Thus, such brackets usually debond from the tooth surface upon receiving a shear force or other force of greater magnitude than the strength of the bond between the tooth and the bracket. In some cases, instead of debonding, such brackets may fracture, destroying the bracket, or transmit the non-corrective force to the tooth, damaging the tooth surface or other part of the tooth and/or causing the patient discomfort. Non-corrective and external forces also may include those resulting from a sudden blow or other impact, which may be applied in virtually any direction. Also, during orthodontic treatment, a corrective force may result in damage to the tooth and/or to the bracket, for example if such a force is incorrectly administered by an orthodontist, or inadvertently misdirected due to orthodontic hardware that has become misaligned or incorrectly oriented. The various forces to which an orthodontic appliance is subjected may vary due to such factors as the relative position of the tooth to which an appliance is attached in the dental arch, the direction and/or strength of the corrective forces exerted on the tooth by the archwire, and so forth.

Figure 14:
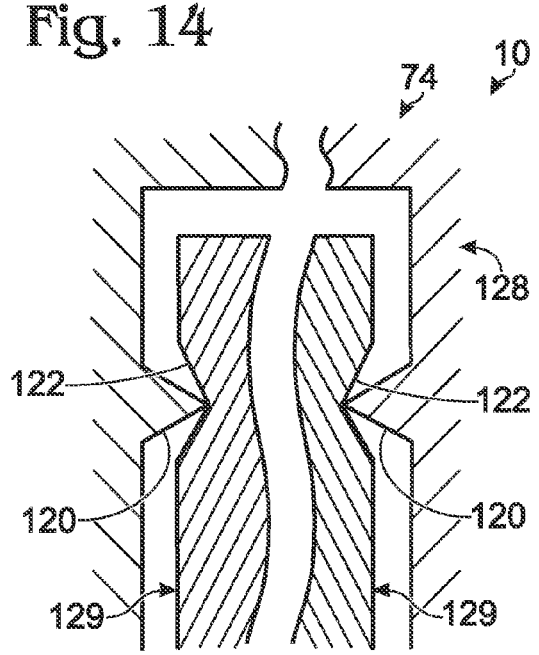
FIG. 14 is a fragmentary, cross-sectional side elevation view of an illustrative, non-exclusive example of a floating hinge assembly of a bracket assembly according to the present disclosure.
Figure 15:
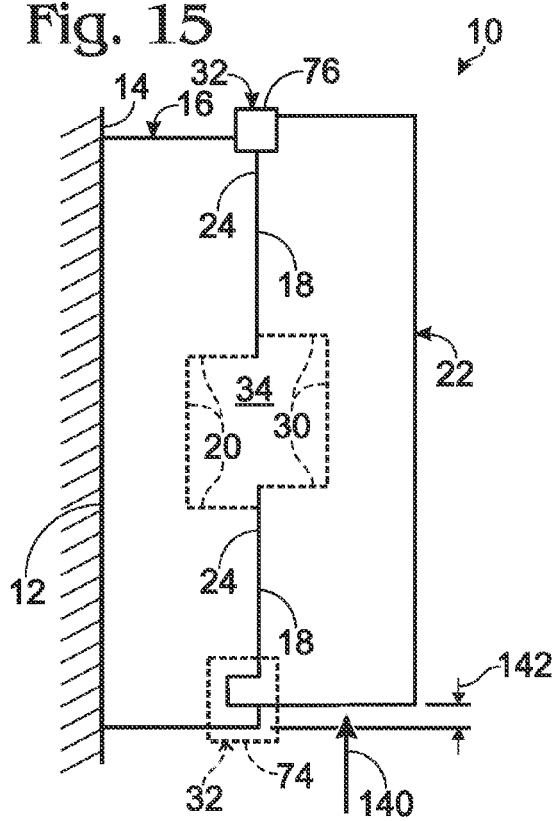
FIG. 15 is a schematic view of an illustrative, non-exclusive example of a bracket assembly according to the present disclosure in which an external mechanical force is applied to the closure.
Figure 16:
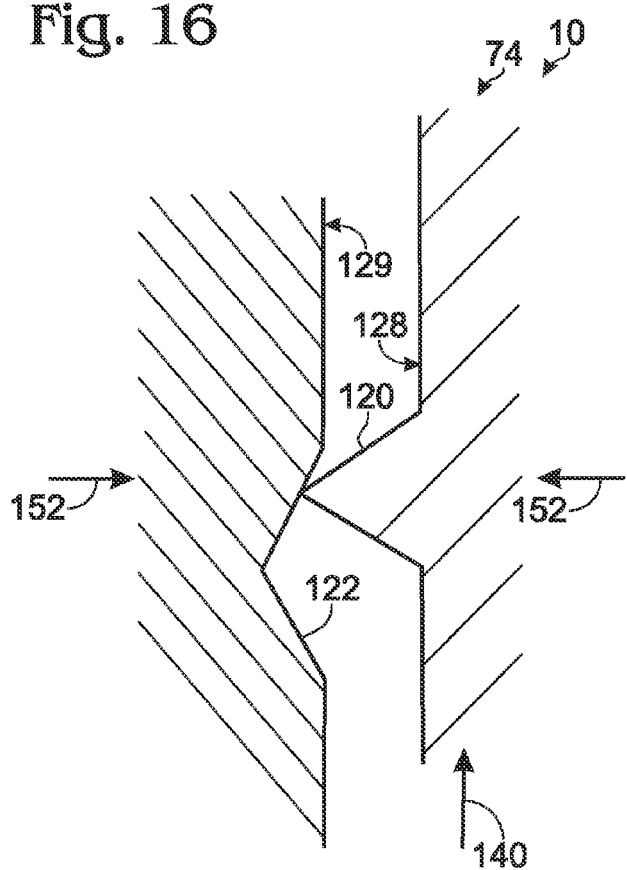
FIG. 16 is a schematic, fragmentary cross-sectional side elevation view of the floating hinge assembly of the bracket assembly of FIG. 15 with the external mechanical force applied to the closure.

As discussed herein, connecting assemblies 32 according to the present disclosure may comprise any suitable configuration for operatively and releasably connecting base 16 with closure 22 or, alternatively, different portions of base 16 or closure 22 with other portions of base 16 or closure 22, respectively, including a hinge, clasp, fastener, set screw, sliding gate, or catch. An illustrative, non-exclusive example of a suitable structure for connecting assembly 32 is hinge assembly 74. An illustrative, non-exclusive example of a hinge assembly 74 according to the present disclosure is shown in FIG. 14 and may additionally or alternatively be described as a floating hinge or floating hinge assembly 74. In FIG. 14, hinge assembly 74 comprises an outer, or male, portion 128 that includes a pair of cone-shaped projections 120, and an inner, or female, portion 129 that includes a pair of cone-shaped indentations 122. The hinge may be designed such that outer portion 128 applies a compressive force to inner portion 129 via the cone-shaped projections. Thus, the apex of cone-shaped projections 120 will naturally migrate to, and be biased toward, the apex of cone-shaped indentations 122, thereby maintaining a fixed hinge geometry when no external loads are applied to the hinge, or to another portion of the bracket assembly 10. However, if an external force is applied to the hinge, such as via another portion of the bracket assembly 10, the apex of the cone-shaped projections may "float" (i.e., translate or otherwise move or be moved) away from the apex of the cone-shaped indentations, for example, when the force is greater than a displacement force. If the external force is not large enough to completely displace the cone-shaped projections from the cone-shaped indentations (i.e., less than a removal force), the hinge will return automatically to its original geometry when the external force is removed, thereby providing the hinge with some amount of non-destructive shock-absorbing capability. This is shown schematically in FIGS. 15 and 16. In FIG. 15, an external force 140 is applied to closure 22, causing it to shift a small amount 142 relative to base 16. FIG. 16 is a schematic, fragmentary cross-sectional view of hinge 74. As shown, the magnitude of external force 140 is large enough to displace cone-shaped projection 120 relative to cone-shaped indentation 122; however, it is not large enough to completely displace the cone-shaped projection from the cone-shaped indentation. That is, the force 140 is larger than zero and is larger than or equal to a displacement force, but it is less than a removal force.

As also shown in FIG. 16, the displacement of the outer portion 128 relative to the inner portion 129 creates a restoring force 152, which serves to press the outer portion toward the inner portion. Thus, when external force 140 is removed, the apex of cone-shaped projection 120 will return to the apex of cone-shaped indentation 122, as discussed herein.

If the magnitude of the external force is large enough to displace the tip of the cone-shaped projections from the cone-shaped indentations, which may be described as being greater than or equal to a removal force, the hinge may "pop apart," and/or otherwise separate, which may result in the bracket assembly being configured to an open configuration. While the hinge may then need to be reassembled, it may not be damaged and this additional ability to non-destructively absorb external forces may minimize the potential for bond failure and/or damage to the bracket assembly caused by larger external forces that may be applied to the bracket assembly.

Figure 17:
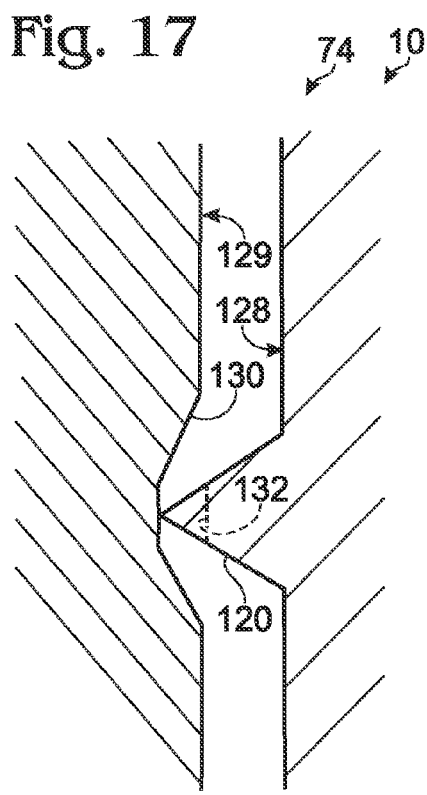
FIG. 17 is a schematic, fragmentary cross-sectional side elevation view of an illustrative, non-exclusive example of a floating hinge assembly in which the cone-shaped indentation comprises a truncated cone.

Numerous variations of the described hinge assembly 74 are possible without departing from the scope of the present disclosure. For example, in FIG. 14 the cone-shaped projections are included on outer portion 128 and a vector drawn along the cone axis from the base of the cone to its apex will generally point toward the apex of the other cone-shaped projection (i.e. the cones point toward each other). It is within the scope of the present disclosure that the cone-shaped projections be included on inner portion 129 and that the cones point away from each other, that the cones point in the same direction, and/or that the hinge assembly comprise more than two cone-shaped projection and cone-shaped indentation pairs. Hinge assembly 74 also may comprise other geometric shapes and still be within the scope of the present disclosure, including truncated cones, cones with base shapes other than circular, partial spheres, etc. In addition, the shapes of the projection and the indentation need not be the same. An illustrative, non-exclusive example of these variations is shown in FIG. 17, where the cone-shaped indentations comprise truncated cones 130. Additionally or alternatively, cone-shaped projections 120 may comprise truncated cones, as schematically indicated at 132. These truncated cone embodiments may have certain benefits, such as decreased wear on the apex of the cone(s) and/or the ability of the hinge to "float" or otherwise permissibly move while the bracket assembly is in its closed configuration, such as within a region defined by the flat top of the truncated cone 130, thus providing for limited and defined "free" motion of the cap with respect to the base in at least one dimension.

Hinge assembly 74 also may be designed to facilitate non-destructive disassembly of the cap from the base. For example, the cone-shaped indentations may be in communication with channels that extend from the cone-shaped indentation to an edge. Thus, by sliding the cone-shaped projections along the channels until they reach the edge, the two parts may be readily separated. As a further example, when the base contains the cone-shaped indentations and the cap contains the cone-shaped projections, channels in the base may be in communication with both the cone-shaped indentations and a base slot surface that serves to define the archwire passage. Thus, by placing the bracket assembly in the open configuration and removing an associated archwire from the base slot surface, the cone-shaped projections may readily slide along the channels until the cone-shaped projections reach the base slot surface, facilitating controlled separation of the closure from the base. However, with an associated archwire in place, the closure may not readily separate from the base.

Another illustrative, non-exclusive example of connecting assemblies 32 according to the present disclosure may include a pin-shaped hinge assembly. A pin-shaped hinge assembly may include a pin operatively attached to closure 22 and received within a slot, defined by base 16, and allows closure 22 to rotate relative to base 16 about the axis of the pin. The slot may be slightly larger than the pin to allow for some translational motion of the pin relative to the slot, thus providing the pin hinge with a defined amount of play or give. Additionally, the base of a pin-shaped hinge assembly may be sealed by a hinge seal to prevent the buildup of foreign material, such as calcium and/or calculus, within the hinge body. The hinge seal, when present, may include any material suitable to seal the hinge, including a combination of adhesion promotion structure and the adhesive or cement used to attach base 16 to tooth 14.

Numerous variations on the illustrative examples of hinges discussed herein may be utilized without departing from the scope of the present disclosure. For example, while a sealed hinge is discussed with reference to a pin-shaped hinge assembly, an unsealed hinge may be used. In addition, it is within the scope of the present disclosure that a hinge pin be part of base 16, while a hinge slot be part of closure 22. Alternatively, the hinge pin and/or the hinge slot may be separate components that are operatively attached to either the base or the closure, respectively.

Referring back to FIGS. 11-13, connecting assemblies 32 and/or 32' may additionally or alternatively comprise clasp 76 and/or fastening structures 110. The clasp and/or fastening structures may have any suitable form that provides for repeated, non-destructive coupling and decoupling of the structures. This coupling and decoupling may be in response to a user-applied force, such as an orthodontist transitioning the bracket assembly from the closed configuration to the open configuration, or it may be in response to an unexpected external force, such as a non-corrective force that is applied (intentionally or unintentionally) to the bracket. For example, a clasp 76 according to the present disclosure may readily decouple in response to a specific series of user-applied forces, such as pushing the closure toward the base and then applying a force to the clasp structure. Illustrative, non-exclusive examples of clasp and fastening structures according to the present disclosure include a hook and ledge structure, in which the hook is accepted around the ledge to hold the clasp or fastening structure in the closed configuration. Alternatively, the cone-shaped hinge structure discussed above may serve as both a hinge and a clasp or fastening structure.

Clasp and fastening structures according to the present disclosure may be designed to minimize or otherwise reduce the force required to transition the structures between the open and closed configurations, thus reducing the forces applied to a patient's teeth and increasing the patient's comfort level. As illustrative, non-exclusive examples, this may be accomplished by locating the structures proximate one side of the bracket assembly, by specific designs that minimize the forces required, by requiring a specific series of actions in order to transition the structure between the open and closed configurations, as discussed above, and/or through the use of other design features that serve to minimize the required transition forces.

As discussed herein, connecting assemblies 32 may be configured to disengage responsive to a force applied to the bracket assembly, such as a non-corrective force that exceeds a predetermined value. For example, if the predetermined value is less than the force sufficient to debond the base from the tooth, the connecting assemblies may be configured to allow the closure to break away from the base responsive to the aforementioned force, rather than permit such a force to cause the orthodontic appliance to break away from the tooth.

In contrast to bracket assemblies according to the present disclosure that include separate bases and closures, orthodontic brackets of monolithic body construction may cause damage to a tooth during debonding. Moreover, even if such a monolithic bracket debonds from a tooth without damage to either the tooth or to the bracket, the tooth surface may be abraded or otherwise damaged by repeated debonding and reattachment of the bracket. Similarly, a conventional orthodontic bracket will require cleaning and preparation of at least one, or both, of the bracket and tooth surface prior to reinstallation of the bracket. Reinstallation also requires careful positioning of the bracket by an orthodontist to reinstall the bracket in the correct location on the tooth and/or relative to other orthodontic brackets.

A bracket assembly 10 with a connecting assembly 32 according to the present disclosure may, but is not required to, protect against inadvertent damage to a tooth such as may be caused by external or non-corrective forces. Different configurations of connecting assemblies 32 may be adapted to release upon application of a force of a predetermined value, such as a value less than a force sufficient to debond the base from the tooth, and/or upon application of a force applied in a predetermined direction. A force greater than a predetermined value that is applied to a closure engaged with a base may simply dislodge the closure and leave the base attached to the tooth, rather than debond the entire orthodontic appliance from the tooth. A releasable configuration may reduce tooth damage by reducing or completely preventing transfer of mechanical force to the tooth or gums, which may be the case with a conventional bracket that is either dislodged as a unit or which does not dislodge and thereby transmits the applied force to the patient's tooth.

Self-ligating bracket assemblies 10 according to the present disclosure that include a connecting assembly 32 configured to releasably, or removably, engage a closure with a base also may, but are not required to, reduce interruptions in orthodontic treatment. For example, an orthodontic bracket of monolithic body construction may accidentally debond from a tooth in response to an applied force such as those described above, necessitating a session of orthodontic maintenance in which the bracket is rebonded to the tooth in order to resume orthodontic treatment. A connecting assembly that allows the closure to disengage from the base responsive to a force may be configured to be readily re-engaged, which may allow for a reduction in and/or elimination of chair time associated with bracket repairs for an orthodontic patient.

The components and/or structural features of base 16 and closure 22 may be configured as desired to enable repeated engagement and disengagement of the assemblies, without destruction or deterioration to any of the components of the bracket assembly caused by engaging or disengaging the connecting assembly, such as during installation and throughout the duration of orthodontic treatment. In particular, connecting assembly 32 may be configured to be reusable after being disengaged, for example by being fabricated to remain structurally intact upon engagement and disengagement. Thus, for example, an orthodontist may install several bracket assemblies 10 to the teeth of a patient, for orthodontic treatment, without having to replace components that become damaged due to disengagement during the period of the treatment. Instead, the orthodontist, or in some embodiments even the patient, may reengage any detached components, resuming treatment. Accordingly, the components, or assemblies, of bracket assemblies 10 according to the present disclosure are adapted to be repeatedly disengaged and reengaged without destruction of the components, or assemblies. For example, the closure of a self-ligating bracket assembly 10 according to the present disclosure may be adapted to be disengaged from a corresponding base that is coupled to a tooth in a patient's mouth. Should the closure be disengaged from the base, such as described herein, neither the base nor the closure is damaged or otherwise rendered unable to be used as part of bracket assembly 10 according to the present disclosure. Accordingly, these components of the bracket assembly may be reengaged, and thereby reused. However, it is not a requirement for a bracket assembly 10 to always have its base and closure reengaged for reuse of both components in all embodiments and at all times. For example, during orthodontic treatment, in some situations it may be desirable to intentionally disengage the base and closure of a bracket assembly 10 according to the present disclosure and to reengage the base, which is still coupled to a tooth, to a different closure. It is further within the scope of the present disclosure, though not required, that the disengaged closure may be reengaged with a different base for further use. Therefore, bracket assemblies 10 may be described as being "reusable" even though reuse is not required to all embodiments or in all applications.

Some embodiments of bracket assemblies 10 according to the present disclosure may include an alignment feature, such as connecting assemblies that are configured to engage only when urged together in one or more predetermined orientations. Such an alignment feature may reduce the time required to properly couple the portions together during a session of orthodontic maintenance, such as by facilitating correct alignment of a base and a closure. Such a feature may optionally allow an orthodontic patient to correctly re-engage a closure that has become disengaged from a base without having to consult an orthodontist.

Some embodiments of bracket assemblies 10 according to the present disclosure additionally or alternatively may include visual indicia to visually indicate if the connecting assemblies are misaligned, disengaged, or otherwise incorrectly engaged. Such visual indicia may assist a patient or an orthodontist in determining if a closure of a bracket assembly is incorrectly engaged or aligned with a corresponding base. This determination may be useful during installation of the closure, and/or thereafter, such as when a patient's mouth is subject to a force that potentially may have decoupled the connecting assemblies of one or more bracket assemblies in a patient's mouth. For example, the visual indicia may include a colored surface on a connecting assembly, mating surface, and/or other part of the orthodontic appliance. Such a colored surface may be positioned to be occluded from view when the closure is properly engaged with the base, such that a visible colored surface may alert a patient or an orthodontist that a closure should be re-engaged, or correctly aligned, with its corresponding base. Additionally or alternatively, when the closure 22 of a self-ligating bracket assembly 10 according to the present disclosure is configured to be selectively displaced from a nominal, or default, closed configuration (such as responsive to forces applied to a floating hinge thereof), and/or to be selectively retained in a selected one of a plurality of closed configurations, visual indicia optionally may be used to indicate this relative positioning of the closure with respect to the base of the bracket assembly.

In FIG. 18, a schematic example of a bracket assembly 10 according to the present disclosure is shown that includes a base 16 and a closure 22 that is releasably coupled to the base by a connecting assembly 32. Base 16, closure 22, and connecting assembly 32 may have any suitable configuration and structure, such as disclosed, illustrated, and/or incorporated herein. As schematically shown in FIG. 18, at least a portion of the base that faces away from the tooth 14 to which the bracket assembly is coupled includes visual indicia 168 that is covered or otherwise occluded from view by the closure. FIG. 19 schematically illustrates the bracket assembly of FIG. 18, with the closure displaced from its position shown in FIG. 18, thereby exposing visual indicia 168. In the illustrated schematic example, the closure has been translated vertically relative to the properly installed position shown in FIG. 18. In some embodiments, the closure may be restricted to one or more of lateral displacement, vertical displacement, and/or rotational displacement.

It is within the scope of the present disclosure that a bracket assembly 10 according to the present disclosure may, but is not required to, include a tether device that is adapted to couple the closure with the base or the archwire even when the closure and base are disengaged from each other. Such a tether device may be described as providing a physical linkage between the closure and the base or the closure and the archwire. This linkage may simply interconnect the assemblies, such as in the form of a flexible linkage that extends between the assemblies to ensure that a disengaged closure is not lost.

As discussed herein, some embodiments of connecting assemblies 32 may include a feature to restrict or prevent some relative movement of the engaged connecting assemblies and/or the base and the closure, while permitting relative movement of the connecting assembly and/or base and closure in another predetermined direction or manner. Such controlled movement may assure that corrective forces exerted by the archwire on the bracket assembly are not misdirected due to improper alignment of the components of the assembly, while simultaneously allowing the connecting assembly to disengage responsive to a non-corrective force applied to the appliance.

For example, once properly aligned and engaged, translational movement in an occlusal and/or gingival direction may be prevented, with translational movement in a labial direction (i.e., generally perpendicular to the tooth surface) permitted. In other words, connecting assembly 32, such as hinge structure 74, clasp structure 76, or fastening structure 110 may allow the engaged assemblies to resist relative sideways, or lateral, movement, and instead direct such forces to disengage the cap from the base in a direction generally perpendicular to the tooth. In other words, some embodiments of bracket assemblies 10 according to the present disclosure may be configured to disengage the connecting assemblies in one or more predetermined directions while resisting forces received from other directions, and/or may redirect such received forces in order to disengage the connecting assemblies rather than allow such forces to cause debonding of the base and/or be transmitted to the tooth.

Bracket assemblies (including self-ligating bracket assemblies) 10 according to the present disclosure may optionally include an insert 102, which additionally or alternatively may be referred to as a corrective insert, a prescriptive insert, a prescription-altering insert, and/or as a closure insert. This insert may serve functional and/or aesthetic purposes and is shown schematically in FIG. 1. As schematically illustrated in FIG. 1, optional insert 102, when coupled to a bracket assembly 10, may extend into the archwire passage 34, and thereby alter the profile or cross-sectional profile, of the archwire passage. Accordingly, in such embodiments, the insert may be described as altering the prescription of the archwire passage and/or of the bracket assembly.

Additionally or alternatively, as schematically represented in dash-dot lines in FIG. 1, some prescriptive inserts 102 according to the present disclosure may be configured to be coupled to the bracket assembly in a plurality of prescription-defining positions, with each of the prescription-defining positions defining a unique prescription of the archwire passage and/or of the bracket assembly. Accordingly, a prescription may be selectively adjusted based on the position or orientation of the optional prescriptive insert relative to the archwire passage, for example, based on the extent to which the insert extends into the archwire passage and thus on the modified, or altered, profile of the archwire passage. Stated differently, as a result of an altered or modified profile of an archwire passage, the associated archwire, when appropriately positioned within the archwire passage will impart a different prescriptive force to the bracket assembly and thus to the patient's tooth, than if the prescriptive insert were not present and/or in a different position. Some bracket assemblies 10 according to the present disclosure may be described as including ratcheting inserts and/or adjustable inserts, such that the insert, when present, may be selectively pivoted and retained in a selected position of the plurality of prescription-defining positions.

Likewise, it is also within the scope of the present disclosure that the closures of some self-ligating bracket assemblies 10 may be configured to be selectively retained in a selected one of a plurality of predetermined, or predefined, closed configurations relative to the base of the bracket assembly, such as with each of the plurality of closed configurations defining an archwire passage with a different cross-sectional configuration, and thus being configured to create a different prescriptive force when an associated archwire is received into the archwire passage. Such a multi-position, adjustable, and/or ratcheting, closure may, for example, be selectively retained in the selected closed configuration within a range, or series, of predefined closed configurations, by one or more suitable latches, detents, clips, catches, or other retaining structure that is configured to releasably engage and selectively retain the closure. Such retaining structure may be a portion of the base of the bracket assembly or may be a separate portion of the bracket assembly that is selectively coupled to the base and closure to retain the closure in a selected closed configuration.

Additionally or alternatively, a bracket assembly or bracket without an insert may be described as defining a first archwire passage, and when an insert is selectively utilized with the bracket assembly or bracket, the insert and bracket may collectively define a second archwire passage that is described as overlapping with the first archwire passage, for example including at least one common archwire contacting surface between the two uniquely defined archwire passages. In such an example, the archwire passages may be described as defining unique prescriptions of the bracket assembly or bracket.

In some bracket assemblies according to the present disclosure, a prescriptive insert may be required to properly define a prescription for the respective bracket assembly. That is, some bracket assemblies according to the present disclosure may not be configured to define an archwire passage that is configured to receive corrective forces from an associated archwire, unless a prescriptive insert is present to define force-receiving surfaces of the archwire passage. However, it is also within the scope of the present disclosure that bracket assemblies may define an archwire passage adapted to receive corrective forces from an associated archwire, even when a prescriptive insert is not present, and may define a second, or altered, archwire passage when a prescriptive insert is present to receive different forces from an associated archwire.

FIGS. 20-24 schematically illustrate illustrative, non-exclusive examples of the prescription-altering effects of prescriptive inserts 102 according to the present disclosure. In FIG. 20, an insert 102 is shown to be housed in closure 22. It is within the scope of the present disclosure that an insert may form, define, and/or change the shape of at least one of the surfaces of archwire passage 34, with these surfaces optionally being referred to as insert archwire contacting, or engaging, surfaces. This may thereby cause the corrective force generated by the archwire and the bracket assembly to change from the forces generated when the insert is not used. Accordingly, it is within the scope of the present disclosure that a bracket assembly 10 may be operative to apply corrective forces to a tooth during orthodontic treatment regardless of whether or not the bracket assembly includes insert 102. That is, as discussed herein, a bracket assembly according to the present disclosure may include an archwire passage that defines a prescription without the addition of an optional insert, and when the optional insert is utilized, a different prescription may be defined. Moreover, by selectively using and/or interchanging inserts of different sizes and/or shapes, these corrective forces may be adjusted, or changed, by an orthodontist without requiring removal of the bracket assembly from the tooth or reshaping or replacement of the archwire. As discussed herein, also within the scope of the present disclosure are prescriptive inserts that may be selectively positioned, or oriented, in more than one position relative to the closure and/or base, with each position defining a unique prescription for the bracket assembly.

The closure and/or the insert may include insert retaining structures 170 that are adapted to selectively retain the insert within the closure. The insert may be retained within the closure using any suitable structure, such as a set screw or other positive mechanism that locks the insert in place, a press or taper fit between the insert and the closure, and/or physical structures on at least one of the insert and the closure that serve to limit the motion of the insert when accepted in the closure and/or snap or lock the insert into place. The insert also may simply be held in place by closed bracket assembly 10. Also shown in FIG. 20 is optional insert locating groove 172. The insert locating groove may be used to assist in accurate placement of the bracket assembly on the tooth surface during initial installation and adhesion of the base to the tooth, may be designed to accept a bracket positioning instrument, and/or may visually represent the location of the archwire passage 34.

As discussed, insert 102 may serve functional (i.e., corrective) purposes within the bracket assembly. In FIG. 20, this is illustrated by the fact that the insert protrudes into archwire passage 34 and may serve to further define and/or restrict the location of an associated archwire within the archwire passage. In FIG. 20, the presence of the insert on the top and left surfaces of archwire passage 34 will serve to press the archwire down and to the right. Consequently, the archwire will tend to exert an additional corrective force on the tooth relative to the force applied to the tooth by the archwire when the insert is not present. Thus, the use of inserts may allow an orthodontist to fine-tune and/or otherwise specifically adjust the corrective forces applied to individual teeth by an archwire that applies corrective forces to many of the patient's teeth. Additionally or alternatively, the geometry of archwire passage 34 may be such that, without an insert in place, the archwire may float or otherwise be loosely positioned within the archwire passage, allowing bracket assembly 10 to act as a passive orthodontic appliance, such that forces are not applied to the bracket assembly by the archwire. With an insert in place, the archwire may be further constrained such that bracket assembly 10, together with insert 102, exerts a force on the archwire, and vice versa, and acts as an active orthodontic appliance. The selective use of inserts also may allow the bracket assembly to function as a hybrid appliance, in which it is active in certain correctional force directions and passive in others.

FIGS. 21-24 further schematically illustrate how inserts 102 may be used to change forces applied to a patient's tooth. In FIG. 21, an insert that surrounds the archwire on three sides (e.g., the top, bottom, and right, as viewed from the illustrated orientation) is shown. This style of insert may decrease the size of archwire passage 34 and cause bracket assembly 10 to become an active orthodontic appliance, whereas the bracket assembly may be a passive appliance when the schematically illustrated insert is not present. In contrast, FIG. 22 illustrates a configuration in which insert 102 protrudes into one side of archwire passage 34, which as illustrated is a right side that is generally opposed to and/or faces the base of the bracket assembly. This insert may contact the archwire, causing the archwire to apply an additional corrective force that is directed to the right in FIG. 22. In FIG. 23, the insert protrudes into the top (as viewed from the illustrated orientation) of the archwire passage, and therefore this insert may cause the archwire to apply an additional corrective force that is directed upward relative to the force if an insert were not present. Finally, FIG. 24 illustrates an insert that serves to twist, or angle, the archwire passage, and thus an associated archwire, in a clockwise direction. This type of insert may be used to apply a torsional force to the tooth. In this example, an associated archwire will apply a torsional force in a counter-clockwise direction. The insert may be box-shaped (i.e., with generally flat archwire passage defining surfaces), as shown, but also may simply include one or more points of contact between the insert and the archwire that serve to twist the archwire within the archwire passage.

The insert configurations shown in FIGS. 22-24 are only four potential embodiments and are merely schematically represented. It is within the scope of the present disclosure that inserts 102 may be designed to apply any desired corrective force or combination of forces, also known as the insert prescription, to a tooth, including tip, torque, and/or rotation forces applied to change the angulation, inclination, rotation, height and/or location of the tooth in order to move the tooth toward an optimal occlusion. As used herein, tipping forces refer to forces applied to the tooth in the mesio-distal direction. Thus, tipping forces may impact angulation. Torsional forces refer to forces applied to the tooth by an archwire that is in torsion within the archwire passage. Thus, torsional forces tend to rotate the tooth in the bucco-lingual directions and may impact inclination. Rotational forces refer to applied forces that tend to rotate the tooth about its long axis. Thus, while a particular insert cross-section is shown in the Figures, it is within the scope of the present disclosure that other insert cross-sections may be used and/or that the insert cross-section may change along the length of the insert, allowing the bracket assembly to apply forces to the tooth in all three dimensions. For example, tipping forces that impact angulation may be generated by inserts that cause the archwire passage to be at an angle with respect to the occlusal plane, with angles between $-6°$ and $+6°$ being common but not exclusive examples. Torsional forces that impact inclination may be generated by inserts that twist the archwire along its long axis, as shown in FIG. 24, with torsional angles between $-10°$ and $+10°$ being common but not exclusive examples. Rotational forces may be generated by inserts that cause the archwire passage to be at an angle with respect to the surface or the plane of the tooth, with angles between $-6°$ and $+6°$ being common but not exclusive examples. Inserts 102 may include any combination of the above, such as, for example, a tip of $+2°$, a torsion of $-6°$, and a rotation of $+0°$.

In addition to the use of inserts (and optionally, interchangeable inserts) to change the forces applied to individual teeth, it is within the scope of the present disclosure that a set, or system, of bracket assemblies 10 according to the present disclosure may include a plurality of interchangeable bases and a plurality of interchangeable closures, with the plurality of interchangeable bases and closures configured to direct corrective forces differently from each other. Such a set may allow an orthodontist to adjust the manner in which corrective forces are directed to a particular tooth, both during the initial positioning of the base and subsequently through the use of alternative caps, without removing the base from the tooth, and without reshaping, replacing, or otherwise reconfiguring the archwire. The use of inserts 102 may allow additional fine-tuning of the forces applied to a tooth.

An illustrative, non-exclusive example of an orthodontic treatment method suitable for use with a bracket assembly according to the present disclosure may include selecting one of a plurality of bases, bonding the attaching surface of the base to a tooth or a band that encircles a tooth, selecting one of a plurality of closures configured to provide the approximate corrective force desired, selecting one of a plurality of inserts configured to fine-tune the applied corrective force to the desired value, and assembling the closure and the insert on the base. During the course of orthodontic treatment, the corrective forces may be adjusted by replacing the insert with another insert having a different prescription value. The plurality of inserts may include a plurality of incrementally-designed inserts, each having a slightly different prescription value, that allow for the application of varying amounts of torque, tip, and rotation, with incremental changes between minimum and maximum values. For example, torque may be varied between −20° and +20°. Illustrative, non-exclusive examples of torque ranges according to the present disclosure include torque values that are varied from −15° to +15° in 5° increments, −12° to +12° in 3° increments, or −10° to +10° in 5° increments. Tip and rotation may be varied between −12° and +12°. Illustrative, non-exclusive examples of tip and rotation ranges according to the present disclosure include tip and rotation values that are varied from −10° to +10° in 5° increments, −8° to +8° in 4° increments, or −6° to +6° in 3° increments. Values outside of these ranges, and smaller and larger increments, are also within the scope of the present disclosure.

Incremental insert design may allow for the progressive use of inserts with different prescription values throughout the orthodontic treatment process and may significantly decrease the overall time, labor, and patient discomfort associated with a particular treatment. For example, the use of inserts may allow a faster progression from small to large archwire diameters, effectively eliminating the need for one or more archwire changes during the course of the treatment by allowing the orthodontist to fine-tune the applied corrective forces, further constrain the archwire, and/or cause individual bracket assemblies to be active or passive as desired. Additionally or alternatively, during the course of normal orthodontic appliance (bracket) adjustments, inserts may allow an orthodontist to fine-tune the forces applied to individual teeth (such as by using inserts to change the dimensions of individual archwire passages) without (re)bending the existing archwire or requiring a new archwire to be used and thereby decreasing the overall treatment time that otherwise would be needed with conventional brackets.

As discussed herein, base and closure slot surfaces 20 and 30 according to the present disclosure may include additional structure, such as archwire locating structures 84, that are designed to locate the flat surfaces 96 of an archwire 90. These structures, when used in conjunction with inserts as described above, may allow the inserts to alter or otherwise modify the forces applied by the archwire without requiring that archwire passage 34 be significantly larger than archwire 90. This may decrease the overall form factor and/or size of bracket assembly 10. Thus, in FIG. 25, a side view of archwire passage 34 is schematically shown to include archwire locating structures 84, such as convex projections 94 that serve to locate flat surfaces 96 of an archwire 90. Archwire 90 is constrained by archwire passage 34, such as within the illustrated closed boundary, but also may rotate a defined amount in both the clockwise and counterclockwise directions, such as schematically illustrated with archwire 90 in dashed lines. Thus, by varying the geometry of archwire passage 34, including the shape of convex projection 94, the permitted twist in archwire 90 and resultant torque applied to a tooth, together with the overall translational freedom of archwire 90, can be changed. In addition, since the corners of the archwire are not directly constrained by the geometry of the archwire passage, the closure may be allowed to translate to a certain extent without putting forces on the archwire or, alternatively, the archwire may be allowed to translate without putting forces on the bracket assembly. This may increase patient comfort during instances in which external mechanical forces are inadvertently applied to either the archwire or the bracket assembly by increasing the shock-absorbing capabilities of the orthodontic appliance. In FIG. 25, the locating structures 84 and convex projections 94 are schematically illustrated as being defined by the base and/or the closure of the bracket assembly; however, it is within the scope of the present disclosure that one or more (or none) of these structures and projections may be defined by an optional prescriptive insert, when present. Accordingly, in an example of such an embodiment, the bracket assembly may define a passive archwire passage when an insert is not present, and the presence of an optional insert may define more than one optional position for an associated archwire, when the insert is present. Other configurations are also within the scope of the present disclosure.

As discussed herein, an optional insert 102 may additionally or even alternatively serve aesthetic purposes. For example, a front or labial-side view of an insert may include aesthetic components designed to increase the visual appeal of a bracket assembly. These aesthetic components may include any design (or indicia), lettering, numbering, symbols, or logos. The insert and/or closure also may be colored and/or clear and may have the same, complementary, and/or contrasting colors and designs. These aesthetic components may be standard components that are available from the bracket assembly manufacturer or may be custom-created for an individual patient. It is also within the scope of the present disclosure that an insert serves an entirely aesthetic purpose and does not interact with the archwire to modify the corrective forces applied to a tooth.

Inserts 102 according to the present disclosure may be of any suitable shape, size, and/or form factor, such that they provide the desired archwire contacting and/or aesthetic characteristics, and may be of a single or multiple-piece construction. The inserts also may be placed from either the tooth-side or the labial-side and may be contained within the cap, within the base, within both the cap and the base, and/or simply placed around the archwire and retained by the closed bracket assembly. For inserts contained within the closure, placement from the tooth-side and subsequent locking in place when the closure is placed in the closed position may facilitate secure insert mounting. Alternatively, placement from the labial-side may provide a significant clinical advantage in terms of faster positioning and/or prescription changes.

In addition, the archwire-contacting surfaces of the inserts may include archwire locating structures, such as convex projections. Inserts 102 according to the present disclosure may be pre-slotted from the manufacturer and come as a set that allows an orthodontist to select specific prescriptions from a provided prescription series. Alternatively the inserts may be provided as blanks, with the archwire passage being machined or otherwise shaped by the orthodontist to meet the requirements of a particular application or prescription. As a further (optional) alternative inserts may be created in response to a desired prescription, and potentially even created on-site by the orthodontist, such as via the use of 3D (three-dimensional) printers and similar technology.

Several illustrative, non-exclusive examples of orthodontic appliances and bracket assemblies 10 according to the present disclosure are discussed below in connection with FIGS. 26-41. These less-schematic, illustrative examples involve various combinations of the optional structures and features discussed herein, various base and closure geometries, single and multiple-piece closure designs, as well as other features not disclosed in the above discussion. The variety of features, configurations, and structures discussed above are labeled in the individual examples shown below but may not be discussed in detail with respect to each example. Optional alternative configurations and/or variants of several of the examples also are presented. The various embodiments, configurations, and methods disclosed in the paragraphs below are exemplary and should not be considered in a limiting sense, but merely for illustrative purposes of one or more of the aspects of the subject matter described herein. Numerous variations and combinations are possible and considered to be within the scope of the present disclosure.

Figure 27:
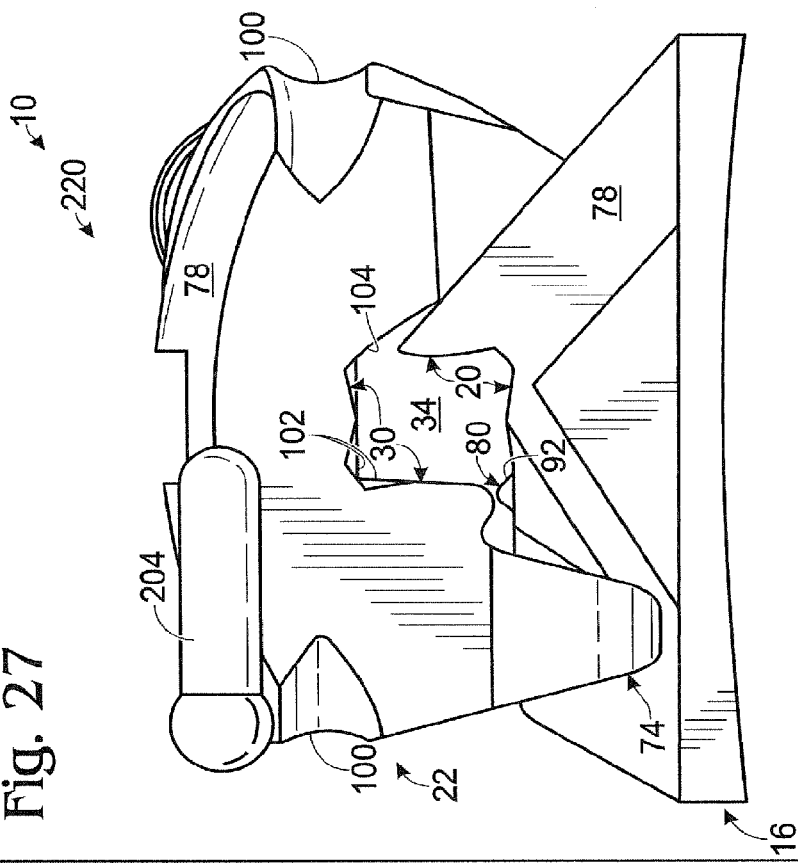
FIG. 27 is an assembled side elevation view of the bracket assembly of FIG. 26, with the bracket assembly illustrated in a closed configuration.
Figure 26:
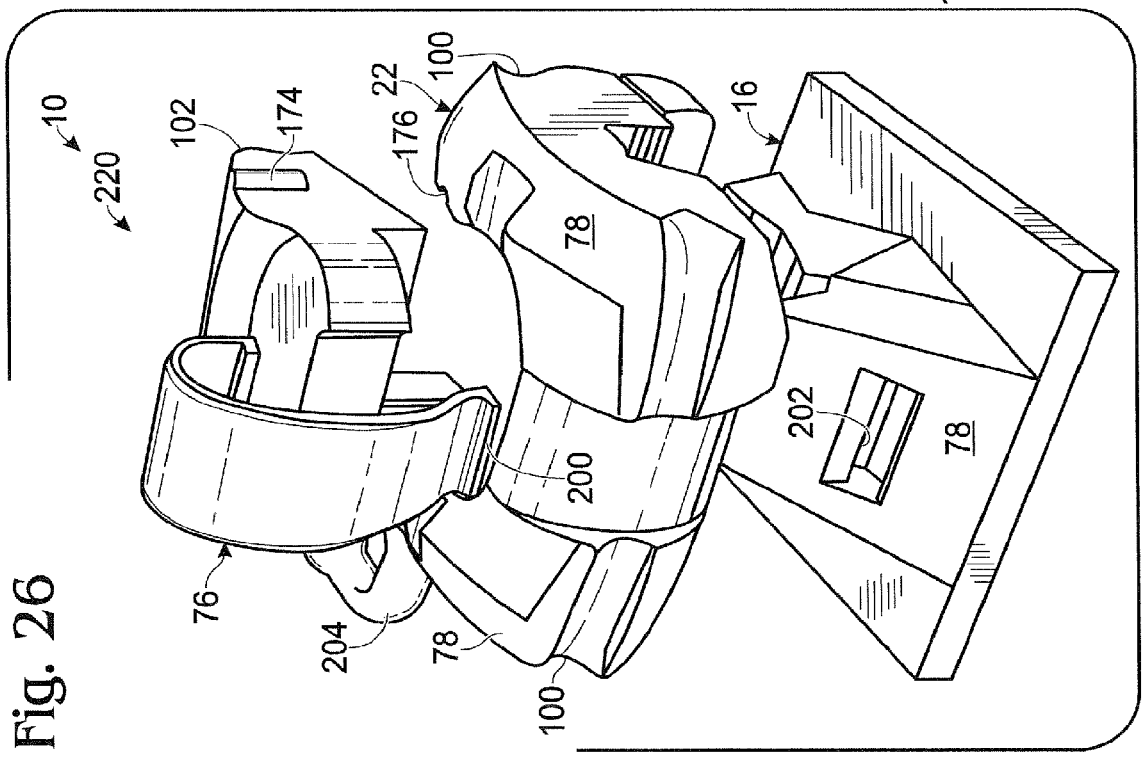
FIG. 26 is an exploded isometric view of an illustrative, non-exclusive example of a bracket assembly according to the present disclosure.

An illustrative, non-exclusive example of orthodontic bracket assemblies 10 according to the present disclosure is shown in FIGS. 26-27 and generally indicated as bracket assembly 220. Bracket assembly 220 provides an illustrative, non-exclusive example of a self-ligating bracket assembly. As perhaps shown most clearly in FIG. 27, two sides of archwire passage 34 of the bracket assembly are defined by base slot surfaces 20 and two sides of the archwire passage are defined by closure slot surfaces 30, similar to the schematic assembly of FIG. 3. Base 16 is configured for operative attachment to a tooth, while, as seen most clearly in FIG. 27, closure 22 hinges from base 16 via hinge structure 74. Although not required to all embodiments, hinge structure 74 may be or include a "floating" hinge, as discussed herein, which enables the closure to translate or otherwise deflect in response to applied external forces, to thereby absorb some or all of these forces (and thus potentially reducing the amount, if any, of the applied external forces that are imparted to a patient's teeth, reducing the potential for the bracket to be damaged, reducing the potential for the bracket to be debonded from the tooth, etc.)

As perhaps best seen in FIG. 26, bracket assembly 220 further includes a clasp 76 that is selectively coupled to the closure and the base to maintain the bracket assembly in a closed configuration. As illustrated, clasp 76 includes a hook, or catch, 200 that is configured to be selectively engaged with a ledge, or detent, 202 on the base of the bracket assembly. Likewise, clasp 76 includes an upper hook, or catch, that is configured to engage the closure to secure the clasp for movement with the closure as the closure pivots relative to the base in an open configuration. Clasp 76 may be transitioned from the closed configuration to an open configuration by applying a force on the closure that is directed toward the base and then pressing in on hook 200. Hook 200 may additionally or alternatively be described as a spring clip or just as a clip. In some applications, an orthodontist, technician, or other operator may utilize a tool to apply at least some of these forces to the clasp, although this is not required to all embodiments. As discussed herein, both clasp 76 and hinge 74 structures also may allow closure 22 to be released from base 16 if a force of large enough magnitude is applied to closure 22 or archwire 90. Force-deflecting and/or force-directing structures 78, in the form of angled surfaces, are present on both the base and the closure and serve to both minimize the impact of these non-corrective forces on the closure, thus minimizing the likelihood that the closure will open and/or detach from the base, and provide a base that is unlikely to debond from the tooth surface.

When closure 22 is a "ratcheting" closure, the plurality of closed configurations may be defined by one or more of a series of spaced-apart detents 202 on the base of the bracket assembly and/or a set of differently sized clasps, such as which may have different lengths between the catches and/or different degrees of resiliency.

As perhaps best shown in FIG. 27, the base further includes an archwire retaining structure 80 in the form of an archwire retaining projection 92. The base and closure also include archwire locating structures in the form of convex projections that serve to locate all four flat surfaces of an associated archwire. The cap further includes closure ligating structures 100, which allow attachment of an orthodontic chain to the bracket assemblies, while minimizing contact between the archwire and the orthodontic chain, thus minimizing friction. The closure also includes cap attachment clearance structure 104, as best seen in FIG. 27, which allows the closure to hinge between the open and closed configurations without contacting an associated archwire, when present.

Bracket assembly 220 further includes a removable (and optional) prescriptive insert 102, which in the illustrative, non-exclusive example comprises a complex geometric shape. The illustrated insert of bracket assembly 220 is placed within closure 22 from the labial-side of the closure and includes male keyed portions 174, which are accepted into female keyed portions 176 within the closure and which serve to lock the prescriptive insert 102 into closure 22. It is within the scope of the present disclosure that the relative locations of the keyed portions may be reversed or varied and/or that other suitable interconnecting structures may be used to selectively couple the insert to the closure. As perhaps best shown in FIG. 27, the insert, when present, serves to further define the shape of archwire passage 34. A wide variety of insert shapes and corrective forces are possible without departing from the scope of the present disclosure, and bracket assembly 220 may be used without an insert. As discussed herein, bracket assemblies 10 according to the present disclosure may include additional structures not disclosed above without departing from the scope of the present disclosure. An example of such an additional structure is shown in FIGS. 26-27, in which bracket assembly 220 is shown to further include a ball hook 204.

Figure 28:
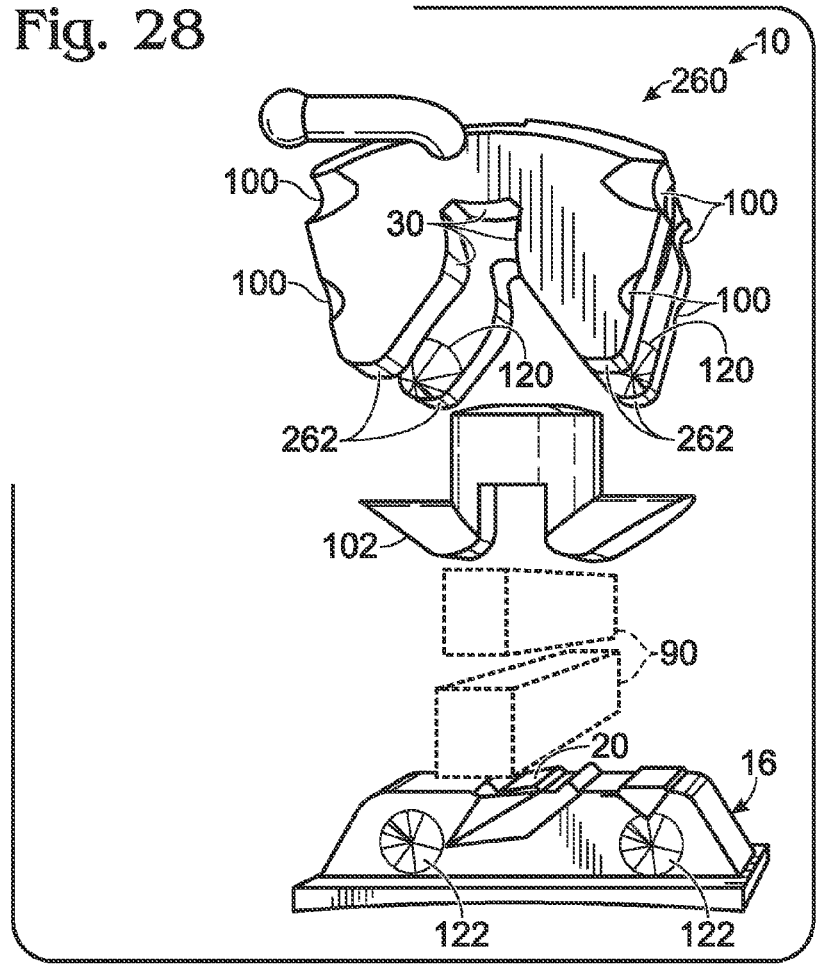
FIG. 28 is an exploded isometric view of another illustrative, non-exclusive example of a bracket assembly according to the present disclosure.
Figure 29:
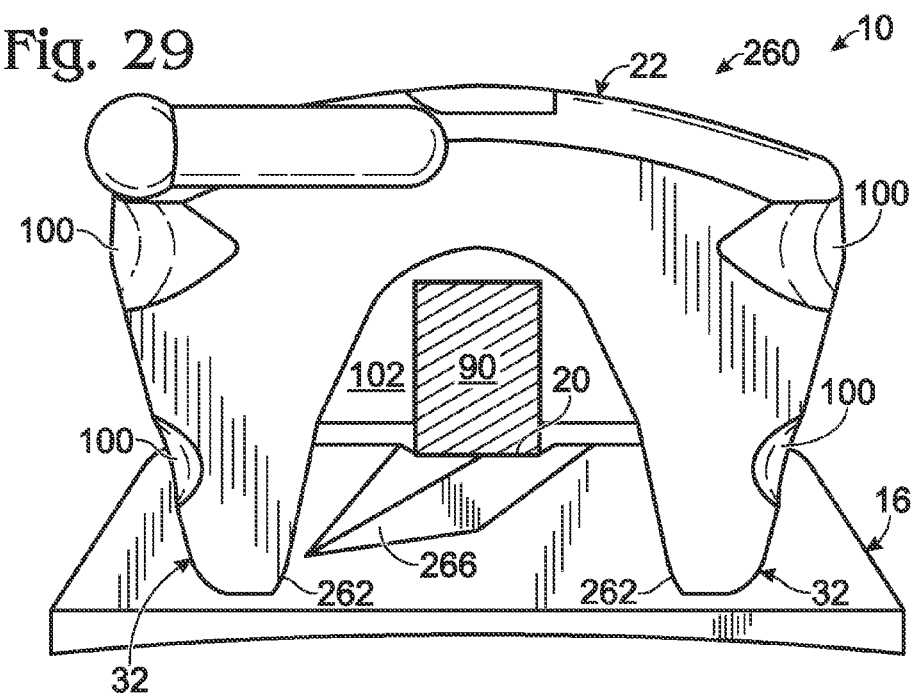
FIG. 29 is an assembled side elevation view of the bracket assembly of FIG. 28, with the bracket assembly illustrated in a closed configuration.

Additional illustrative, non-exclusive examples of orthodontic bracket assemblies 10 according to the present disclosure are shown in FIGS. 28-29 and are generally indicated at 260. FIGS. 28-29 disclose two similar self-ligating bracket assemblies 10. In FIG. 28, one side of the archwire passage is defined by base slot surface 20, and three sides of the archwire passage are defined by closure slot surfaces 30, similar to the schematic assembly of FIG. 4. In FIG. 29, one side of the archwire passage is defined by base slot surface 20, and three sides of the archwire passage are defined by a prescriptive insert 102, without the closure 22 forming, or defining, any archwire contacting surface. Both illustrated examples graphically depict base portions that include one or more projections and/or recesses, thereby providing for a wider range of positions for an archwire within the archwire passage than if the base included only a completely flat surface that defined a wall of the archwire passage. It is within the scope of the present disclosure to include such a flat surface on the portion of the base that defines a base wall, or base side, of the archwire passage, but a more complex surface may permit the bracket assembly to define a wider range of prescriptions.

In both examples of FIGS. 28 and 29, closure 22 is operatively connected to base 16 using connecting assembly 32 in the form of cone-shaped projections 120 and cone-shaped indentations 122. Insert 102, when utilized, is inserted from the tooth side into at least a frictional fit with the closure.

As perhaps best seen in FIG. 28, closure 22 of bracket assembly 260 is somewhat table-shaped and includes legs 262 that extend on opposed sides of the defined archwire passage. The long, slender shape of the legs may provide the closure with a spring-like or resilient character that may serve to absorb external or non-corrective forces in a non-destructive manner. The closure also may include two different sets of closure ligating structures 100. Upper closure ligating structure 100 functions as described herein. Lower closure ligating structure 100, which may be referred to as a closure lock, allows the use of a ligature below the associated archwire to lock closure 22 onto base 16, increasing the rigidity of bracket assembly 260 and allowing the orthodontist to apply larger corrective forces without allowing separation of closure 22 from base 16.

Bracket assembly 260 also may utilize channels 266 defined by the base to facilitate installation and/or removal of closure 22 from base 16 by directing cone-shaped projections 120 toward cone-shaped indentations 122 and/or by allowing cone-shaped projections 120 to more easily separate from cone-shaped indentations 122 through application of an external force in a pre-defined direction. As illustrated, the channels, or recesses, 266 extend from the indentations and define a path through which the corresponding cone-shaped projections may be removed from the indentations, such as responsive to an orthodontist, technician, or other operator urging the projections into the channels and away from the indentations. Although not required, FIG. 29 illustrates that the channels on each side of the base of the bracket assembly may have a different shape and/or orientation relative to the indentations. Such a construction may permit only a pair of the projections to be removed from the corresponding indentations, such as would permit the other set of projections and indentations to function as a hinge (or even a floating hinge) that enables pivotal movement of the closure relative to the base. In such a configuration, the closure could optionally be completely removed from the base by urging the remaining (connected) projections into the corresponding grooves to also free these projections from contact with the indentations, and thereby untethering the closure from the base. It is within the scope of the present disclosure that only one set of such projections are designed to be selectively removed from the corresponding indentations, thereby permitting pivotal movement of the closure relative to the base without permitting complete removal and reattachment of the closure to the base.

FIG. 28 schematically illustrates two archwires 90 of differing cross-sectional areas. In practice, only one archwire may be used; however, the two different archwires illustrate the fact that the use of insert 102 may allow the application of bracket assemblies 10 according to the present disclosure, such as bracket assembly 260, to retain archwires of varying cross-sectional area without the need to replace either base 16 or closure 22. FIGS. 28-29 illustrate that legs 262 of the closure may have various shapes without departing from the scope of the present disclosure. In FIG. 28, legs 262 define closure slot surfaces 30 that define three surfaces of the archwire passage. Thus, closure 22 of FIG. 28 may be utilized with or without an insert 102. In contrast, FIG. 29 shows legs 262 of closure 22 that do not define any closure slot surfaces. In this example, insert 102 may be used to fully define the archwire passage and retain an archwire 90 in place. While an insert may be required to apply corrective forces with the bracket assembly when utilizing cap configurations according to FIG. 29, the comparatively large clearance between closure 22 and archwire 90 provides for a great degree of flexibility regarding the placement of the archwire with respect to bracket assembly 260. Moreover, in some applications, as discussed herein, it may be desirable during orthodontic treatment for one or more of the bracket assemblies to be passive and to not provide corrective forces to the corresponding tooth to which the bracket assembly is attached.

Figure 30:
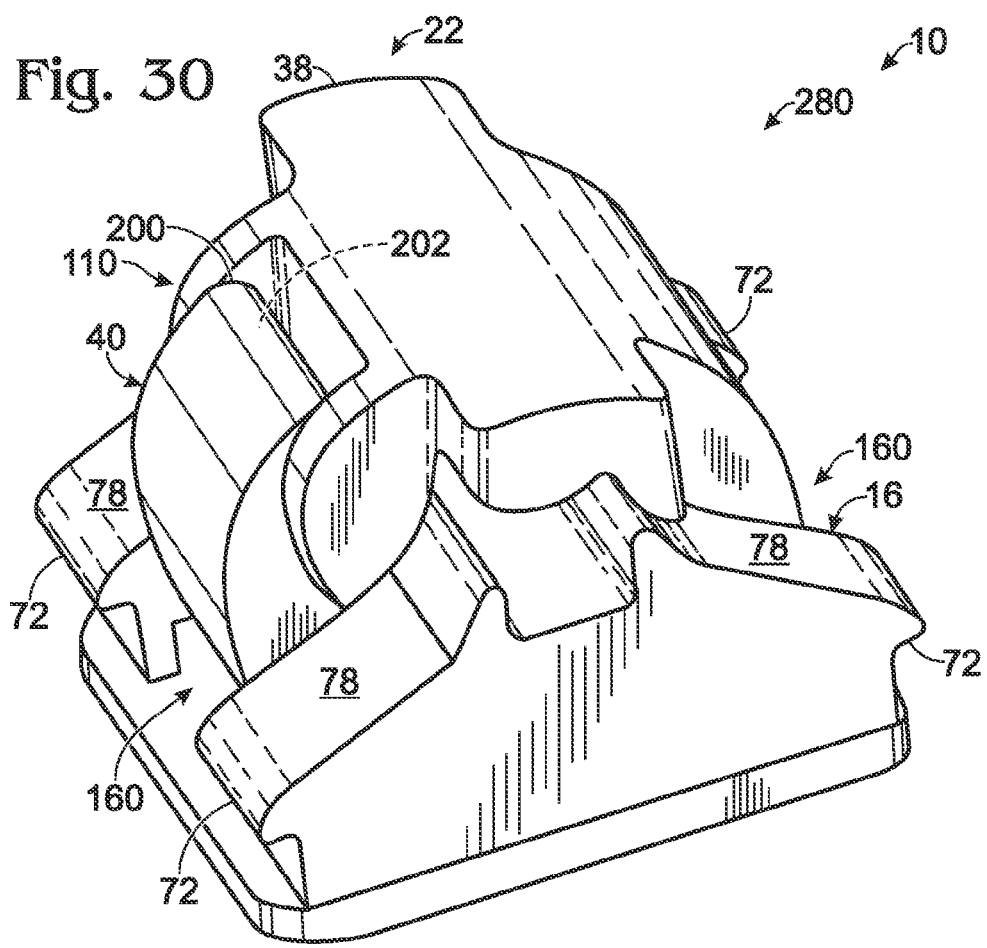
FIG. 30 is an assembled isometric view of another illustrative, non-exclusive example of a bracket assembly according to the present disclosure.
Figure 31:
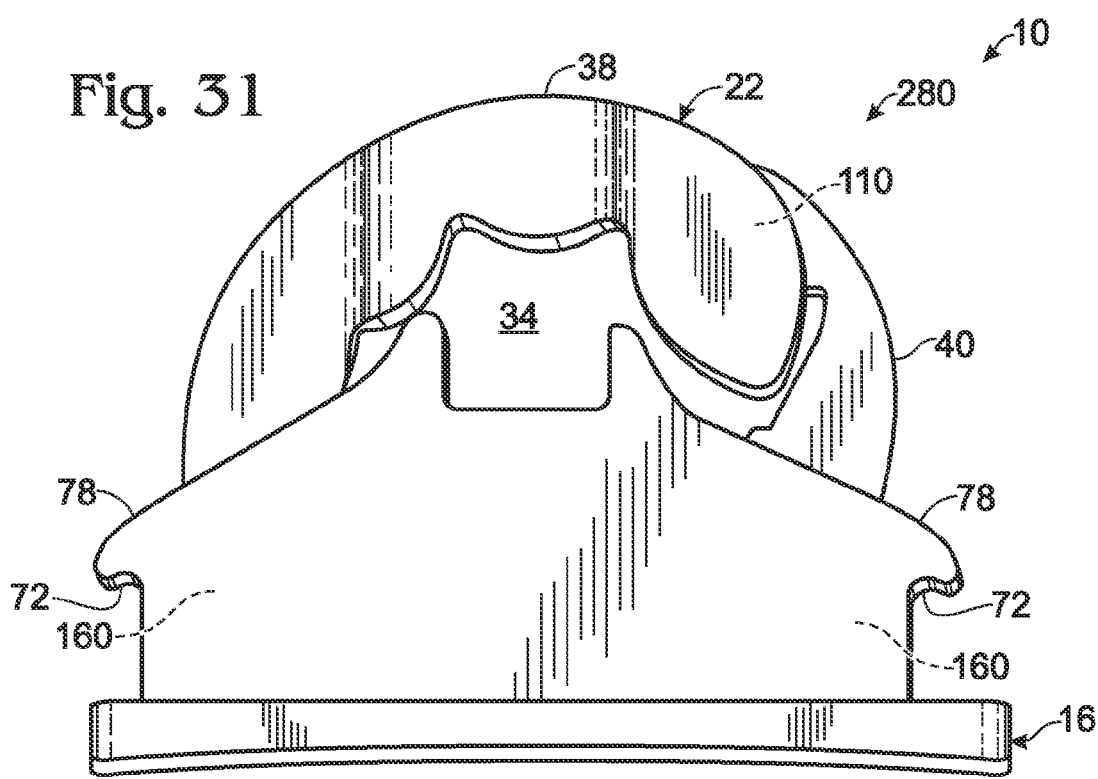
FIG. 31 is an assembled isometric side elevation view of the bracket assembly of FIG. 30, with the bracket assembly illustrated in a partially closed configuration.

Yet another illustrative, non-exclusive example of orthodontic bracket assemblies 10 according to the present disclosure is shown in FIGS. 30-31 and indicated generally at 280. FIGS. 30-31 disclose a bracket assembly 10 in which, as shown most clearly in FIG. 31, base 16 and closure 22 each define one complete side of the archwire passage, and two partial sides, similar to the schematic assembly of FIG. 5. Closure 22 comprises first closure portion 38 and second closure portion 40. Each closure portion hinges from base 16 via pin hinge assemblies 160 and the two closure portions may be connected to each other using fastening structure 110 in the form of hook 200 and ledge 202. Bracket assembly 280 may further include base ligating structures 72 and force-deflecting structures 78. For example the components of the fastening structure may be configured to interlock, or interengage, with each other upon urging of the first and second closure portions together. To release the fastening structure, an orthodontist, technician, or other operator may apply an external force to the closure, such as by pressing upon the first closure portion, pressing upon the second closure portion, inserting a tool to urge the closure portions apart, etc. The location of such an applied opening force may vary depending upon the particular size and configuration of the components of the fastening structure being utilized.

Yet another illustrative, non-exclusive example of orthodontic bracket assemblies 10 according to the present disclosure is shown in FIGS. 32-33 and indicated at 300. FIGS. 32-33 disclose a bracket assembly 10 in which, as most clearly shown in FIG. 33, base 16 defines one side of the archwire passage 34, while closure 22 defines three sides of the archwire passage, similar to the schematic assembly of FIG. 4. Similar to bracket assembly 280, closure 22 of assembly 300 comprises first closure portion 38 and second closure portion 40, each closure portion hinges from base 16 via a hinge, and the two closure portions may be operatively connected to each other using fastening structure 110. Bracket assembly 300 further includes resilient pads 302 that act as springs to selectively keep the fastening structure in a secured, closed configuration and also that dampen external forces applied to the bracket assembly. Resilient pads 302 may comprise any suitable material, including elastomeric cushions, metallic springs, metallic clips, foam pads, shock absorbers, and/or any other structure adapted to provide a resilient, shock-absorbing force.

Figure 34:
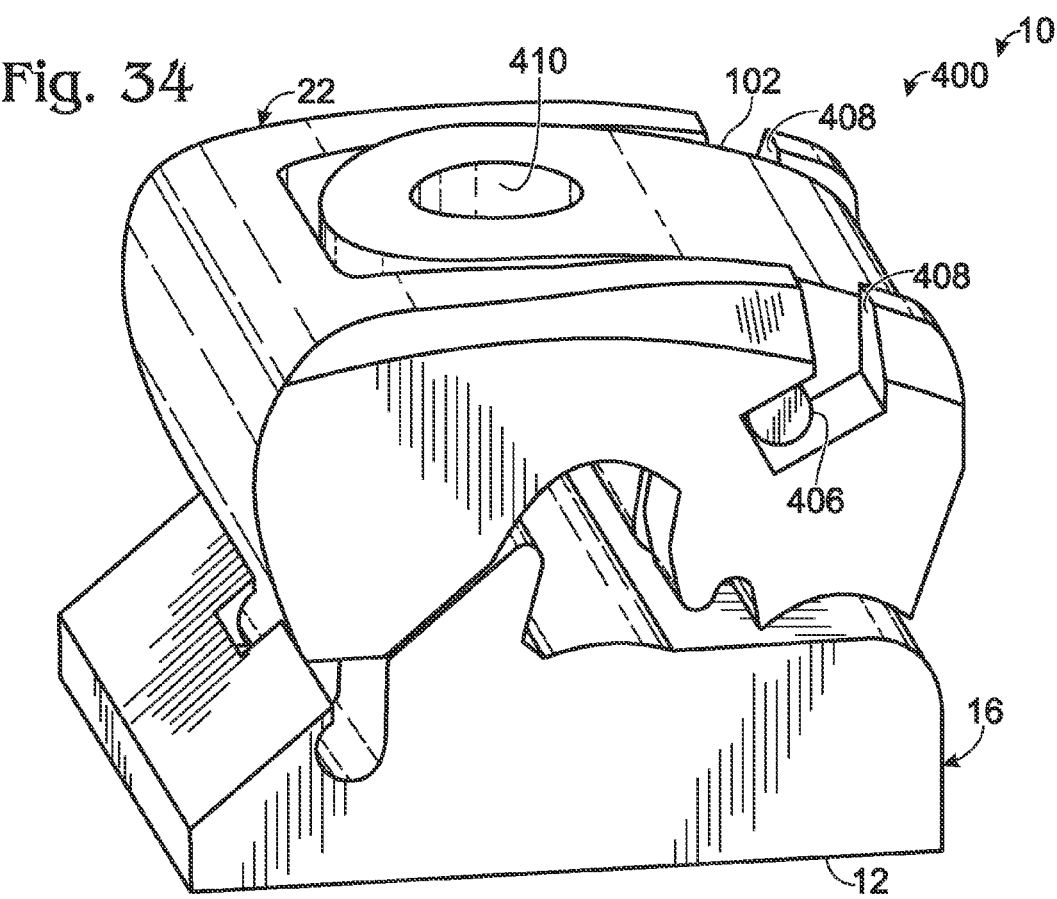
FIG. 34 is an assembled isometric view of another illustrative, non-exclusive example of a bracket assembly according to the present disclosure.
Figure 35:
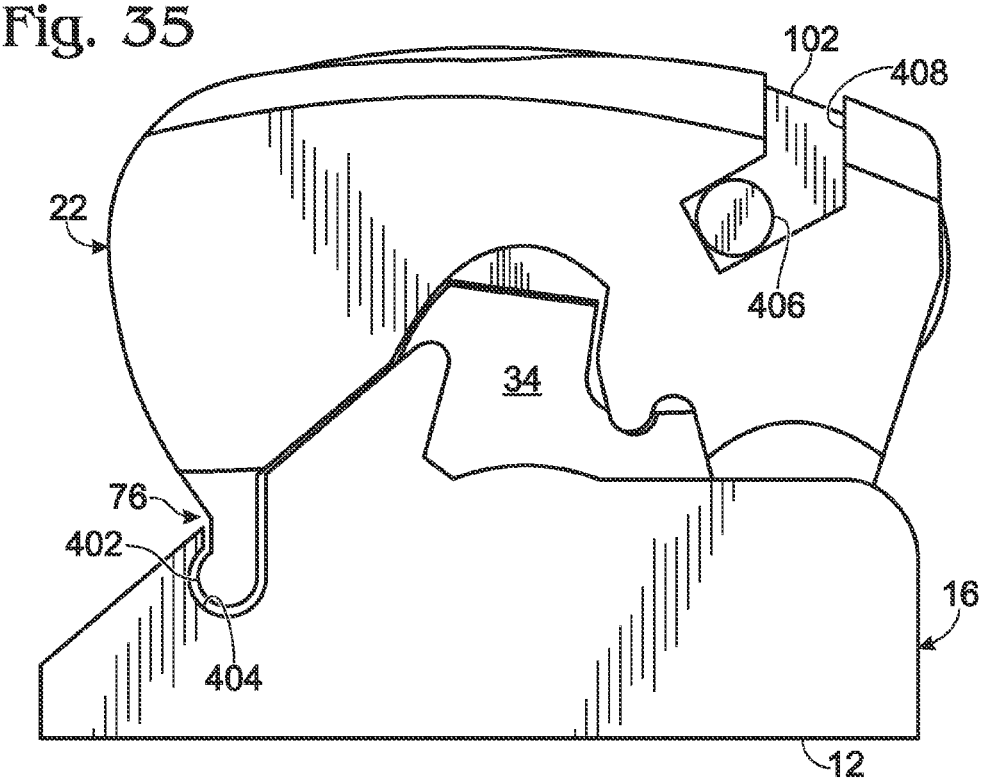
FIG. 35 is a side elevation view of the bracket assembly of FIG. 34.

Yet another illustrative, non-exclusive example of orthodontic bracket assemblies 10 according to the present disclosure is shown in FIGS. 34-35 and indicated at 400. Bracket assembly 400 includes a base 16, a closure 22 that is pivotally coupled to the base, and a prescriptive insert 102 that is received within the closure. The closure includes a pin that is received within a slot of the base to form a hinge assembly. This slot of the base extends from the attaching surface 12 of the base. Accordingly, the closure must be coupled to the base prior to attaching the base to a patient's tooth. The closure of bracket assembly 400 includes a hook, or spring clip, 402 that mates with a groove 404 in a snap-fit arrangement to form a clasp 76, as perhaps best seen in FIG. 35.

Prescriptive insert 102 of bracket assembly 400 includes a pair of laterally extending pins 406 that are received in a pair of channels 408 of the closure. The insert also includes an opening 410 extending from the buccal, or facial, side of the insert. This opening is configured to receive an instrument so that a user may pivot the insert relative to the closure and for removal of the insert from the closure. It is also within the scope of the present disclosure for this opening to be used to receive and secure an aesthetic insert, such as for customization of a bracket assembly by or for a user.

With particular reference to FIG. 35, it can be seen that the prescriptive insert and base of bracket assembly 400 collectively define the archwire passage 34, with the closure of the bracket assembly forming no archwire contacting surface. However, it is within the scope of the present disclosure that bracket assembly 400 may be used without the illustrated prescriptive insert and with other various prescriptive inserts, in which the closure does define an archwire contacting surface of the archwire passage. It is also within the scope of the present disclosure that an orthodontic appliance system may include a plurality of variously configured closures for selective use with the illustrated base of bracket assembly 400. That is, a plurality of closures may be provided for selective coupling to the illustrated base and that may or may not define archwire contacting surfaces either alone or together with an prescriptive insert, and bracket assemblies 400 are not limited to using only the illustrated closure of FIGS. 34-35, as any suitable configuration is within the scope of the present disclosure.

Figure 36:
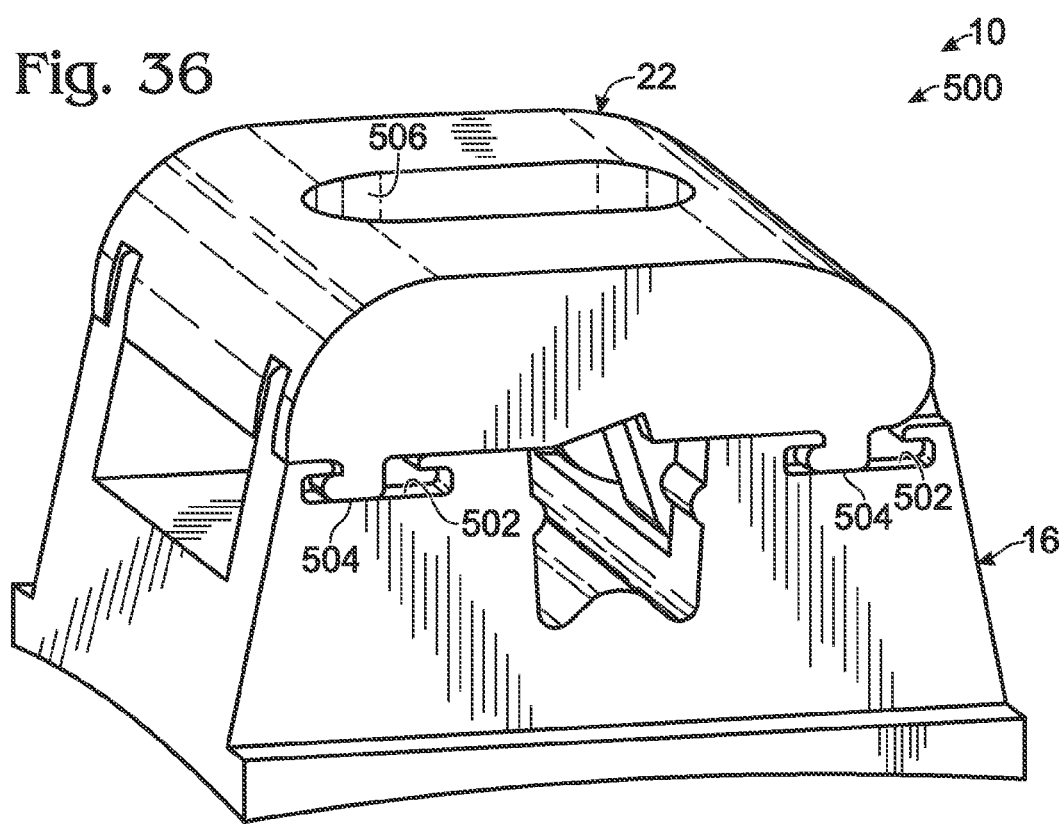
FIG. 36 is an assembled isometric view of another illustrative, non-exclusive example of a bracket assembly according to the present disclosure.
Figure 37:
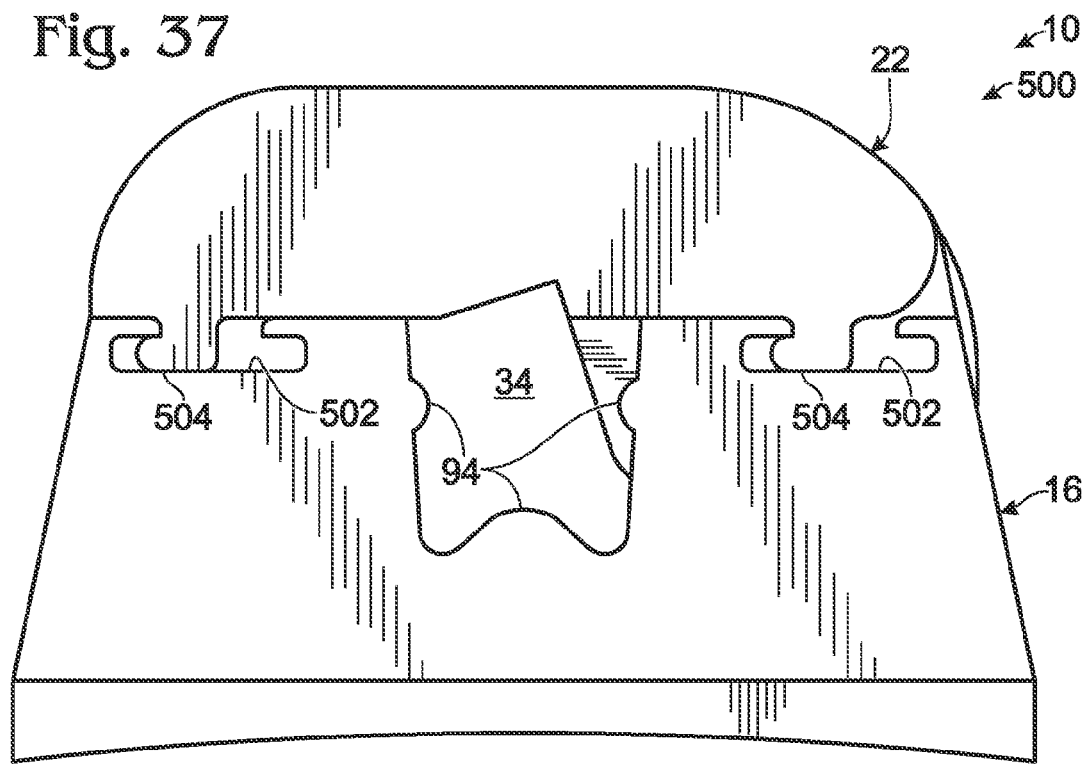
FIG. 37 is a side elevation view of the bracket assembly of FIG. 36.

Another illustrative, non-exclusive example of orthodontic bracket assemblies 10 according to the present disclosure is shown in FIGS. 36-37 and indicated at 500. Bracket assembly 500 includes a base 16 and a prescriptive closure 22. Bracket assembly 500 is an example of a bracket assembly 10 in which a separate prescriptive insert is not utilized. However, more than one closure of bracket assembly 500 may be provided, with various prescriptions defined by the plurality of closures. Accordingly, a closure may be selected based on a desired prescription to be defined by a bracket assembly 500. Additionally, as seen with reference to FIGS. 36 and 37, the base of bracket assembly 500 is laterally symmetrical. Therefore, a single closure may be positioned in one of two directions, effectively defining two unique prescriptions of the bracket assembly depending on the selected orientation of the selected closure.

The base of bracket assembly 500 includes two pairs of T-shaped channels 502, into which corresponding L-shaped hooks 504 of the closure are received. In the illustrated views, these L-shaped hooks extend to the left; however, the closure may be selectively turned around so that the L-shaped hooks extend to the right and still appropriately mate with the base of the assembly and thereby define a second, different prescription.

As perhaps best seen in FIG. 37, the illustrated closure defines two sides of the archwire passage 34 and would impart a counterclockwise twist (as viewed in FIG. 37) on an associated archwire. That is, with the illustrated closure, an associated archwire would impart a clockwise twisting corrective force on the bracket assembly 500. However, if the closure were reversed in its orientation, an associated archwire would impart a counterclockwise twist corrective force. As also seen in FIG. 37, base 16 of assembly 500 includes three convex projections 94 that may engage an associated archwire. However, when the illustrated closure is utilized with the base, the right illustrated projection 94 is prevented from contacting an associated archwire. Various other suitable closures of bracket assemblies 500, on the other hand, may not prevent the right projection 94 from engaging an associated archwire. Various configurations of closures are within the scope of the present disclosure, including configurations in which none, one, two, or all three of the illustrated projections 94 are prevented from engaging an associated archwire, including various closures that define any suitable orthodontic prescription, as discussed herein.

Closure 22 of bracket assembly 500 includes an opening 506 extending from the buccal, or facial, side of the closure. This opening is configured to receive an instrument so that a user may selectively remove the closure from the base and/or position the closure relative to the base. This opening also may selectively receive an aesthetic insert to alter the look of the bracket assembly.

Figure 38:
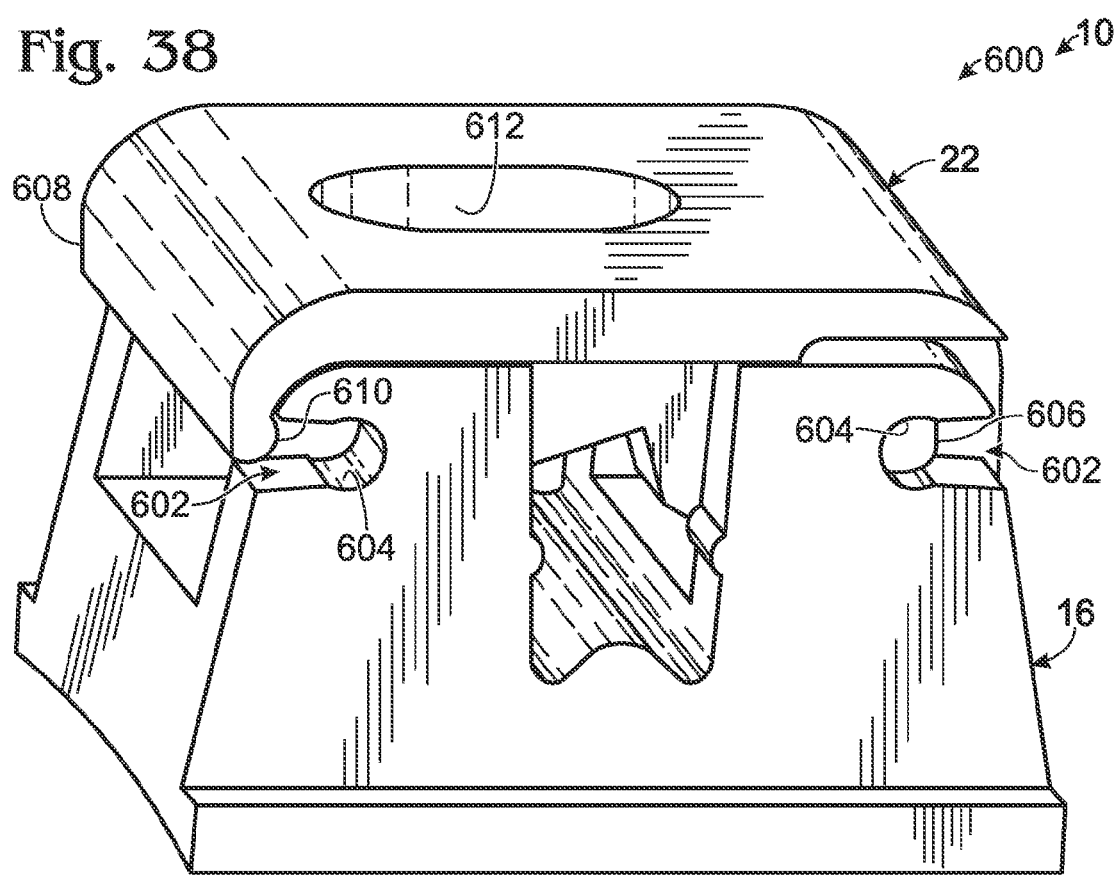
FIG. 38 is an assembled isometric view of another illustrative, non-exclusive example of a bracket assembly according to the present disclosure.
Figure 39:
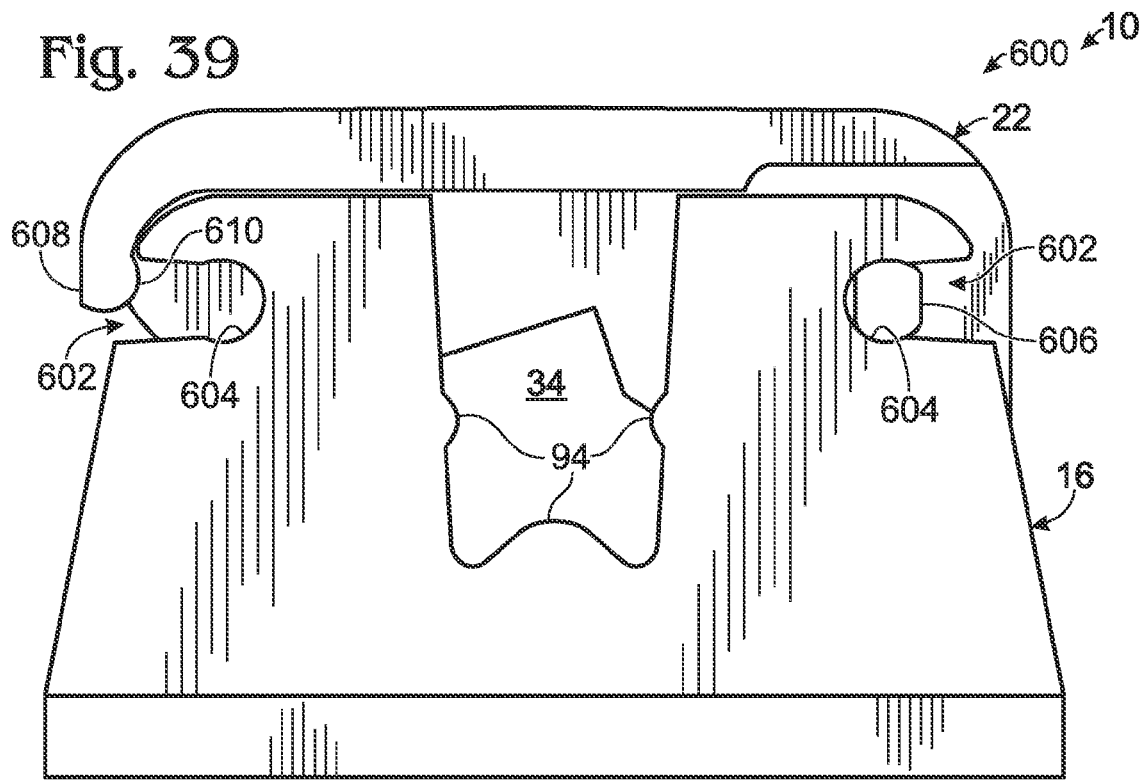
FIG. 39 is a side elevation view of the bracket assembly of FIG. 38.

Another illustrative, non-exclusive example of orthodontic bracket assemblies 10 according to the present disclosure is shown in FIGS. 38-39 and indicated at 600. Bracket assembly 600 is similar to bracket assembly 500, in that it includes a base 16 and a prescriptive closure 22, but does not utilize a separate prescriptive insert. Also similarly, more than one closure of bracket assembly 600 may be provided, with various prescriptions defined by the plurality of closures, and a closure may be selected based on a desired prescription to be defined by bracket assembly 600. Also like bracket assembly 500, the base of bracket assembly 600 is laterally symmetrical, and therefore a single closure may be positioned in one of two directions with respect to the base, effectively defining two unique prescriptions of the bracket assembly depending on the selected orientation of a single closure.

The base of bracket assembly 600 includes two pairs of channels 602 extending from the coronal and apical sides of the base, with each channel including a circular end region 604. The closure of bracket assembly 600 includes a pair of corresponding pins 606 on only one of the coronal or apical sides of the closure (depending on the selected orientation of the closure). The pins may be described as flattened cylinders with opposing flat surfaces, with the distance between the flat surfaces permitting insertion of the pins into channels 602 of the base, for example, with the closure rotated 90 degrees from the orientation illustrated in FIGS. 38-39. When the pins are fully inserted into the channels and the closure is then pivoted to the illustrated position, the circular end regions 604 retain the pins in place and thus the closure in a coupled configuration to the base. The opposite side of the closure from the pins 606 includes a flange 608 with a bulbous end region 610, with the flange additionally or alternatively described as a spring clip. This end region is configured to have a snap-fit arrangement with the edge of the channels 602, as illustrated in FIGS. 38-39. Accordingly, when the closure is pivoted into place, it will secure an associated archwire in the archwire passage 34.

As perhaps best seen in FIG. 39, the illustrated closure defines two sides of the archwire passage and would impart a counterclockwise twist (as viewed in FIG. 39) on an associated archwire. That is, with the illustrated closure, an associated archwire would impart a clockwise twist corrective force on the bracket assembly 600. However, if the closure were reversed in its orientation, an associated archwire would impart a counterclockwise twist corrective force. As also seen in FIG. 39, base 16 of bracket assembly 600 includes three convex projections 94 that may engage an associated archwire. However, when the illustrated closure is utilized with the base, the right illustrated projection 94 is prevented from contacting an associated archwire. Various other suitable closures of bracket assemblies 600, on the other hand, may not prevent the right projection 94 from engaging an associated archwire. Various configurations of closures are within the scope of the present disclosure, including configurations in which none, one, two, or all three of the illustrated projections 94 are prevented from engaging an associated archwire, including various closures that define any suitable orthodontic prescription, as discussed herein.

Closure 22 of bracket assembly 600 includes an opening 612 extending from the buccal, or facial, side of the closure. This opening is configured to receive an instrument so that a user may selectively open the bracket assembly for insertion and removal of an associated archwire. This opening may also selectively receive an aesthetic insert to alter the look of the bracket assembly.

Figure 40:
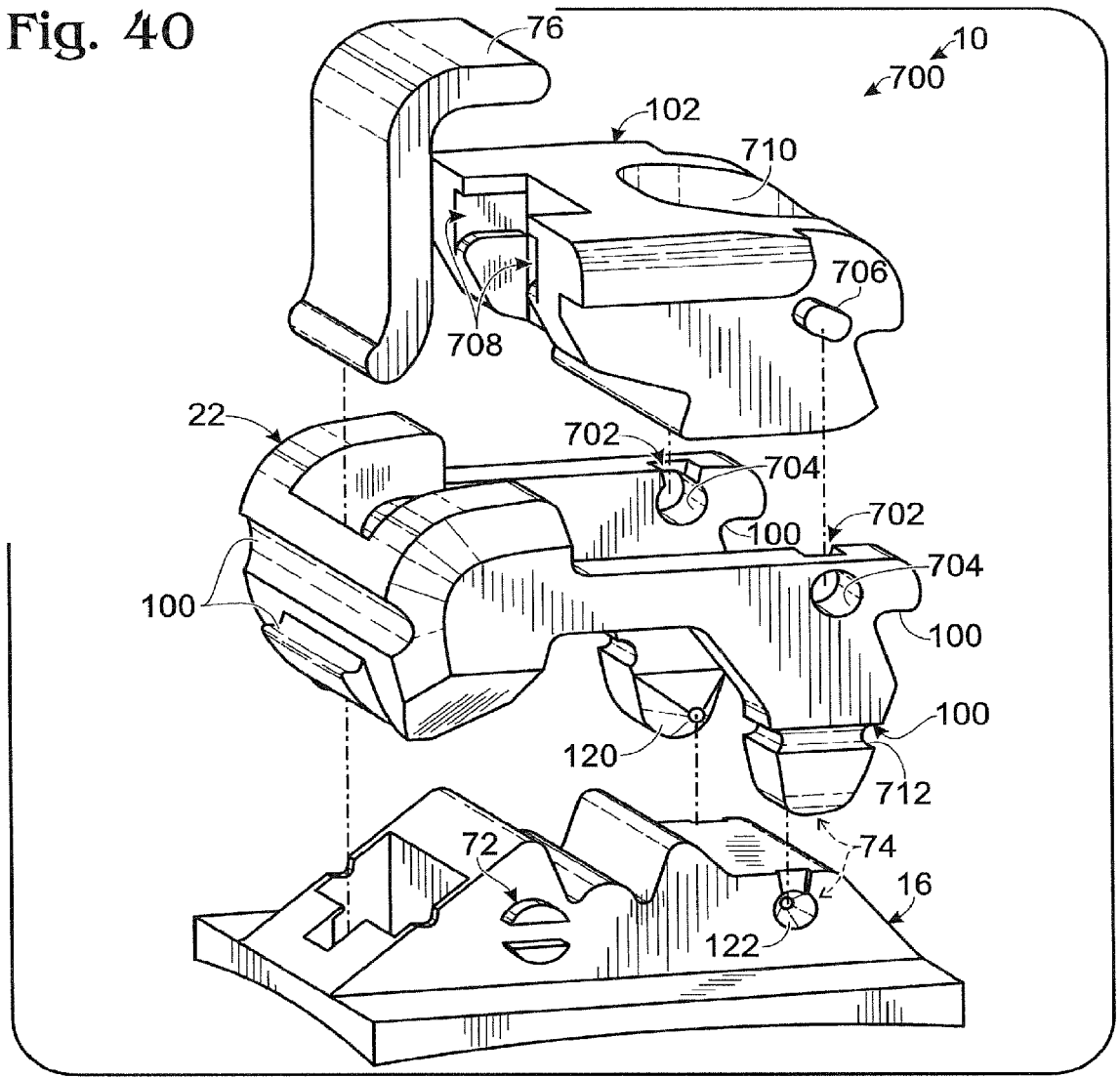
FIG. 40 is an exploded isometric view of another illustrative, non-exclusive example of a bracket assembly according to the present disclosure.
Figure 41:
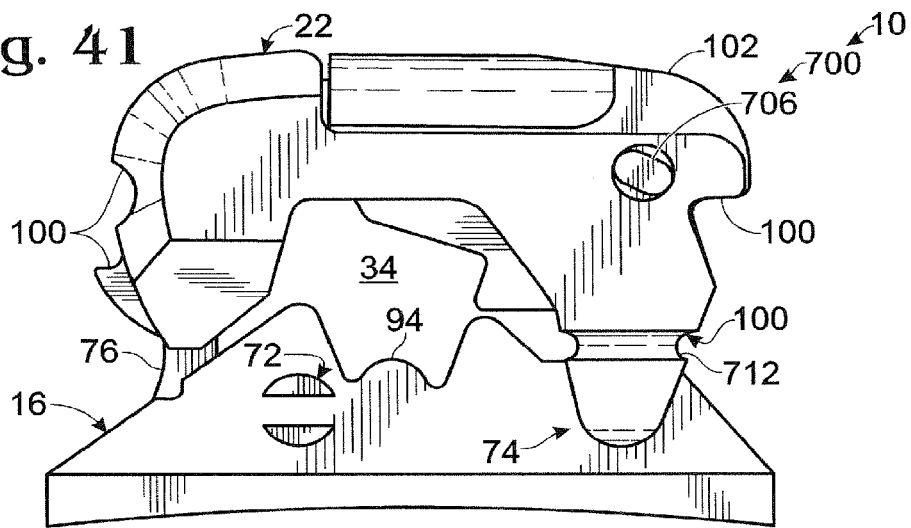
FIG. 41 is a side elevation view of the bracket assembly of FIG. 40.

Yet another illustrative, non-exclusive example of orthodontic bracket assemblies 10 according to the present disclosure is shown in FIGS. 40-41 and indicated at 700. Bracket assembly 700 includes a base 16, a closure 22 that is pivotally coupled to the base, and a prescriptive insert 102 that is received within the closure. Bracket assembly 700 is similar to bracket assembly 220 of FIGS. 26-27, in that the closure and base collectively define a floating hinge 74 having a pair of cone-shaped projections 120 and cone-shaped indentations 122, and a clasp 76 selectively retains the closure in a closed configuration. However, in contrast to bracket assembly 220, which includes a prescriptive insert that slides into place and includes a keyed portion, the prescriptive insert of bracket assembly 700 is pivotally coupled to the closure, somewhat akin to the closure of bracket assembly 600 of FIGS. 38-39. More specifically, the closure of bracket assembly 700 includes a pair of channels 702 that extend from the facial side of the closure and that include circular end regions 704. The prescriptive insert of bracket assembly 700 includes a pair of corresponding pins 706, which may be described as flattened cylinders with opposing flat surfaces permitting insertion of the pins into channels 702 of the closure, for example, with the insert rotated approximately 60 degrees clockwise from the orientation illustrated in FIG. 41. The insert also includes a pair of channels 708 that engage the clasp 76 when the assembly is fully assembled, as best seen in the exploded view of FIG. 40. Accordingly, when the pins of the insert are fully inserted into the channels and the prescriptive insert is rotated counterclockwise (from the perspective of FIG. 41), the insert is retained in place by the clasp.

As perhaps best seen in FIG. 41, the illustrated closure of bracket assembly 700 does not define any archwire contacting surfaces; however, such closures that are configured to engage an associated archwire are within the scope of bracket assemblies 700 according to the present disclosure. In the illustrated example, the base includes a convex projection 94 and collectively defines one side of the archwire passage 34 together with the illustrated prescriptive insert. In the illustrated example, an associated archwire would impart a clockwise twist corrective force on the bracket assembly 700, but other configurations of prescriptive inserts are within the scope of the present disclosure, as are other closures of bracket assemblies 700, such that various orthodontic prescriptions of the bracket assembly may be selectively defined.

The prescriptive insert of bracket assembly 700 includes an opening 710 extending from the buccal, or facial, side of the insert. This opening is configured to receive an instrument so that the insert may be selectively removed from the bracket assembly. This opening may additionally or alternatively be used to selectively receive an aesthetic insert to alter the look of the bracket assembly.

The illustrative bracket assembly 700 also includes optional closure ligating structures 100, including optional ligating structure 712 that is positioned lingual, or palatel, of an associated archwire retained by the bracket assembly. Also included is an optional base ligating structure 72, which may be used to selectively couple one bracket assembly to another, such as an upper bracket assembly to a lower bracket assembly via an elastic band, and/or to secure the closure in a closed configuration.

Figure 42:
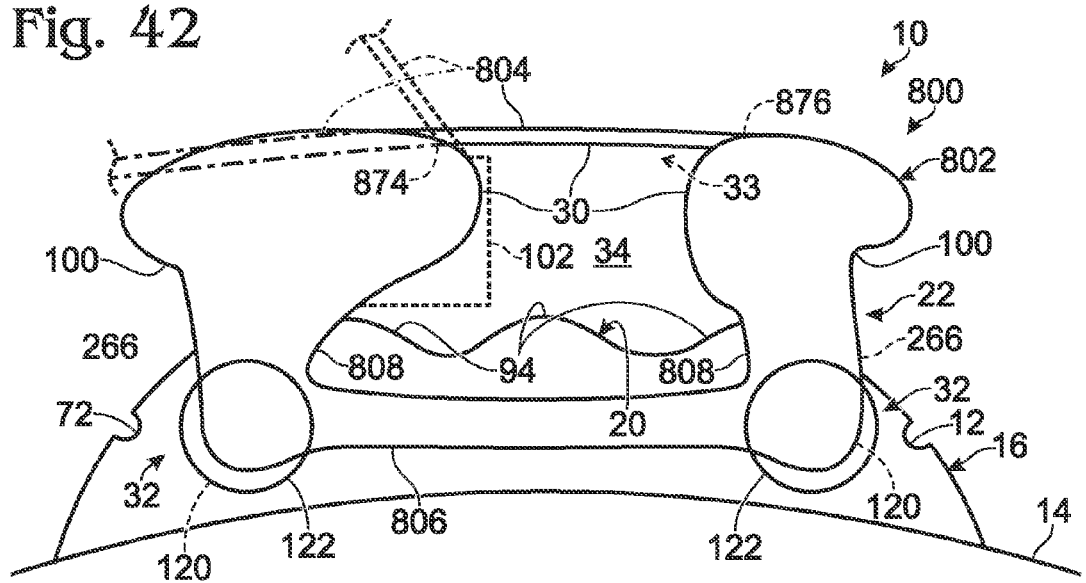
FIG. 42 is a schematic side elevation view of another illustrative, non-exclusive example of a bracket assembly according to the present disclosure.

Another illustrative, non-exclusive example of orthodontic bracket assemblies 10 according to the present disclosure is shown in FIG. 42 and indicated at 800. Like many of the other bracket assemblies 10 disclosed herein, bracket assembly 800 includes a base 16, a closure 22 that is coupled to the base by connecting structure 32. In the illustrated example, connecting structure 32 is shown with the previously discussed cone-shaped projections 120 and indentations 122, but other shapes and configurations of connecting structure may be utilized that also enable the closure to "float" relative to the base, such as in response to forces applied thereto. In other words, connecting structure 32 may be configured to permit the closure to be reversibly displaced within a range of connected positions relative to the base without detaching from the base, and moreover optionally may be biased to automatically return to a nominal, or resting position, when such applied forces are removed.

Optional channels 266 that define paths for selective removal of the closure by disengagement of projections 120 from indentations 122 are also indicated in FIG. 42, although it is also within the scope of the present disclosure that closure 22 is not configured for repeated removal and reattachment to base 16. Specifically, and unlike many of the other previously illustrated examples, closure 22 includes a closure body 802 that itself includes a self-ligating gate 804 that is selectively translated and/or pivoted between open and closed configurations relative to the closure body to respectively enable or obstruct an archwire being inserted or removed through an opening 33 of the archwire passage. Gate 804 may be selectively retained in a closed configuration by a closure clasp 876, and in some embodiments may be selectively pivoted relative to the closure body by a closure hinge 874. Also shown in FIG. 42 is a linkage 806 that selectively interconnects legs 808 of the closure body.

Similar to some of the previously discussed examples, base 16 is illustrated in FIG. 42 to define a base slot surface 20 that includes at least one projection 94, but it is within the scope of the present disclosure that the base slot surface may be planar or otherwise free from projections or indentations and/or that the base may define more than a single surface, or side, of the bracket assembly's archwire passage 34. Additional optional, and previously discussed, structure that is shown in FIG. 42 includes base ligating structure 72, closure ligating structure 100, and insert 102.

Figure 43:
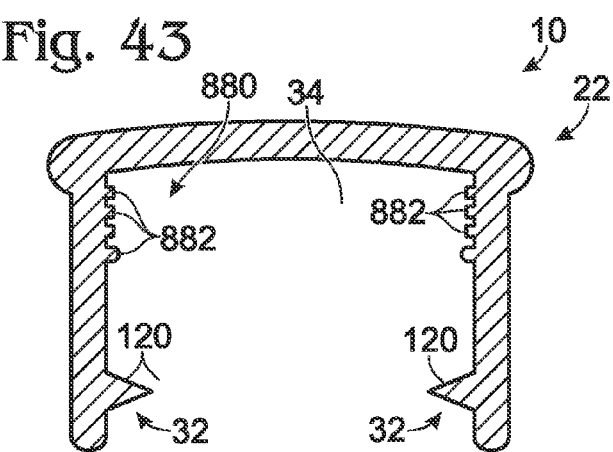
FIG. 43 is a schematic side cross-sectional view of a portion of a closure that may be used with bracket assemblies according to the present disclosure.

An illustrative, non-exclusive example of a closure 22 that is configured to permit selective adjustment, or positioning, of an insert 102 within a series, or range of defined positions is shown somewhat schematically in FIG. 43. As shown, the closure is configured to define at least one, if not several, sides or surfaces of a bracket assembly's archwire passage 34 and includes an internal surface 880 that defines a series of spaced-apart detents, or stops, 882 that are configured to be selectively interengaged with an insert to couple the insert to the closure, such as for relative movement with the closure and/or to alter the prescription defined by the closure. Also shown in FIG. 43 are a pair of opposed cone-shaped projections 120 that form a portion of a connecting assembly 32 to selectively couple the closure to a base of bracket assembly 10, although other suitable connecting structure may be utilized without departing from the scope of the present disclosure.

Figure 44:
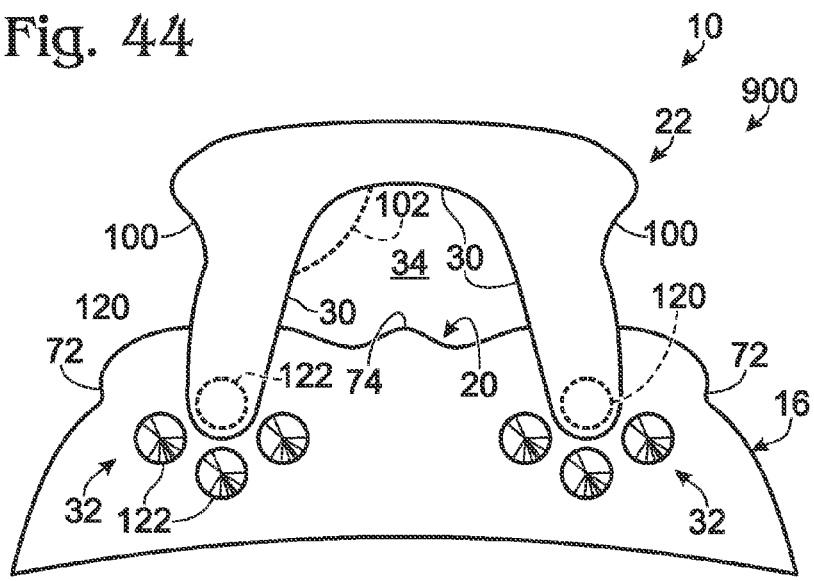
FIG. 44 is a schematic side elevation view of another illustrative, non-exclusive example of a bracket assembly according to the present disclosure.

An illustrative, non-exclusive example of a bracket assembly 10 that includes a closure 22 that may be selectively positioned in a series, or range, of predetermined operative positions relative to a base 16 to which the closure is coupled is shown in FIG. 44 and indicated generally at 900. Specifically, bracket assembly 900 includes a connecting assembly 32 that includes the previously discussed cone-shaped projections 120 and indentations 122; however, base 16 includes a plurality of closed-spaced indentations 122 for each of projections 120. The adjacent indentations 122 of each plurality of indentations optionally may be interconnected by channels or other recesses or grooves along which the tip of the corresponding projection may travel, although this is not required. Although other suitable configurations, relative numbers, and/or relative positions of the components of connecting assembly 32 may be utilized, the "float" provided by the illustrated example may be designed so that the closure may be selectively retained in a plurality of different operative configurations relative to the base, such as depending upon which of the indentations of each plurality of indentations the corresponding projection 120 is coupled. Changing the relative position of the closure results in a change in the dimensions of archwire passage 34. This, in turn, may alter the prescription defined by the bracket assembly (and any optional insert that may be used therewith. Additional optional, and previously discussed, structure that is shown in FIG. 44 includes base ligating structure 72, closure ligating structure 100, and insert 102.

As discussed, bracket assemblies 10 within the scope of the present disclosure may include features, components, and/or variants that are described and/or illustrated herein in connection with one or more of the illustrative, non-exclusive examples that are shown in the accompanying drawings, even if such features, components, and/or variants are not all illustrated together or in the same combination.

Illustrative, non-exclusive, examples of descriptions of some orthodontic appliances within the scope of the present disclosure are presented in the following "enumerated" paragraphs. The following paragraphs are not intended to be an exhaustive set of descriptions, and are not intended to define minimum or maximum scopes or required elements of the present disclosure. Instead, they are provided as illustrative examples of selected orthodontic appliances that are within the scope of the present disclosure, with other descriptions of broader or narrower scopes still being within the scope of the present disclosure.

A1 An orthodontic appliance system, comprising:
a bracket adapted to be coupled to a patient's tooth and including a plurality of bracket archwire contacting surfaces; and
a prescriptive insert adapted to be removably coupled to the bracket and including an insert archwire contacting surface, wherein when the prescriptive insert is coupled to the bracket, the bracket and prescriptive insert collectively define an archwire passage that is adapted to receive an associated archwire, wherein the archwire passage is defined by the plurality of bracket archwire contacting surfaces and insert archwire contacting surface.

A1.1 The orthodontic appliance system of paragraph A1, wherein the archwire passage is a first archwire passage, and wherein when the prescriptive insert is not coupled to the bracket, the bracket alone defines a second archwire passage that is adapted to receive the associated archwire, wherein the second archwire passage shares at least one common surface with the first archwire passage.

A1.1.1 The orthodontic appliance system of paragraph A1.1, wherein when the prescriptive insert is coupled to the bracket, the prescriptive insert prevents at least one of the plurality of bracket archwire contacting surfaces from engaging the associated archwire when the associated archwire is received in the first archwire passage.

A1.1.1.1 The orthodontic appliance system of paragraph A1.1.1, wherein when the prescriptive insert is coupled to the bracket, the prescriptive insert prevents at least two of the plurality of bracket archwire contacting surfaces from engaging the associated archwire when the associated archwire is received in the first archwire passage.

A1.1.1.2 The orthodontic appliance system of paragraph A1.1.1, wherein when the prescriptive insert is coupled to the bracket, the prescriptive insert prevents some but not all of the plurality of bracket archwire contacting surfaces from engaging the associated archwire when the associated archwire is received in the first archwire passage.

A1.1.2 The orthodontic appliance system of any of paragraphs A1.1-A1.1.1.2,
wherein when the bracket is coupled to a tooth, when the prescriptive insert is coupled to the bracket, and when the associated archwire is received in the first archwire passage, the associated archwire imparts a first prescriptive force; and
wherein when the bracket is coupled to a tooth, when the prescriptive insert is not coupled to the bracket, and when the associated archwire is received in the second archwire passage, the associated archwire imparts a second prescriptive force that is different than the first prescriptive force.

A1.1.3 The orthodontic appliance system of paragraphs A1.1-A1.1.2, wherein the first archwire passage overlaps with the second archwire passage.

A1.2 The orthodontic appliance system of any of paragraphs A1-A1.1.3, further comprising a plurality of prescriptive inserts each adapted to be removably coupled to the bracket to collectively define with the bracket a unique archwire passage.

A1.3 The orthodontic appliance system of any of paragraphs A1-A1.2, wherein the bracket is a self-ligating bracket and includes:
a base adapted to be coupled to a patient's tooth;
a closure coupled to the base for selective movement relative to the base for selective insertion and removal of the associated archwire.

A1.3.1 The orthodontic appliance system of paragraph A1.3, wherein the closure defines at least one surface of an archwire passage.

A1.3.2 The orthodontic appliance system of any of paragraphs A1.3-A1.3.1, wherein the closure is adapted to move among a range of positions relative to the base and to be selectively secured in a plurality of orientations within the range of positions, wherein each of the plurality of orientations of the closure at least partially defines a unique cross-sectional profile of an archwire passage.

A1.3.2.1 The orthodontic appliance system of paragraph A1.3.2, wherein the closure has a ratcheting configuration relative to the base.

A1.3.3 The orthodontic appliance system of any of paragraphs A1.3-A1.3.2.1, further comprising a floating hinge that couples the closure to the base.

A1.4 The orthodontic appliance system of any of paragraphs A1-A1.3.2.1, wherein the insert is configured to be removably coupled to the bracket in a plurality of prescription-defining positions, wherein a unique archwire passage is defined when the insert is coupled to the bracket in each of the plurality of prescription-defining positions.

A1.4.1 The orthodontic appliance system of paragraph A1.4, wherein each unique archwire passage defines a unique prescription in which a unique prescriptive force is applied to the patient's tooth when the bracket is coupled to the patient's tooth and when the associated archwire is received in the unique archwire passage.

A1.4.2 The orthodontic appliance system of any of paragraphs A1.4-A1.4.1, wherein the insert is configured to be selectively and incrementally translated and/or pivoted into the archwire passage among a range of the plurality of prescription-defining positions.

A1.4.3 The orthodontic appliance system of any of paragraphs A1.4-A1.4.2, wherein in response to selective positioning of the insert among the plurality of prescription-defining positions, a prescription of the orthodontic appliance system is selectively adjusted.

A1.5 The orthodontic appliance system of any of paragraphs A1-A1.4.3, wherein the archwire passage is configured to receive the associated archwire in a plurality of orientations, wherein each orientation defines a unique prescription of the orthodontic appliance system.

A1.5.1 The orthodontic appliance system of paragraph A1.5, wherein the archwire passage includes at least one non-planar surface configured to engage the associated archwire in more than one of the plurality of orientations.

A1.5.2 The orthodontic appliance system of any of paragraphs A1.5-A1.5.1, wherein the archwire passage includes at least one surface that includes a convex surface extending into the archwire passage.

A1.5.2.1 The orthodontic appliance system of paragraph A1.5.2, wherein the convex surface includes an apex, and wherein the archwire passage is configured to selectively receive the associated archwire so that it engages the convex surface on either side of the apex.

A1.6 The orthodontic appliance system of any of paragraphs A-A1.5.2.1, wherein the system includes any of the various features, structures, portions, components, variations, characteristics, etc, of the systems of any of paragraphs A2-E4 (below).

A1.7 The orthodontic appliance system of any of paragraphs A-A1.6, wherein the system includes any of the various features, structures, portions, components, variations, characteristics, etc, of the bracket assemblies disclosed herein.

A2 An orthodontic appliance system, comprising:
a bracket adapted to be coupled to a patient's tooth, wherein the bracket defines an archwire passage for receiving an associated archwire, wherein the archwire passage includes a plurality of archwire bracket surfaces, wherein each of the plurality of archwire bracket surfaces is positioned to engage the archwire when the archwire is received in the archwire passage, and wherein the plurality of archwire bracket surfaces defines a first prescription to impart a first prescriptive force to the patient's tooth when the bracket is coupled to the patient's tooth and when the associated archwire is received in the archwire passage; and
a plurality of prescription-altering inserts, wherein each of the plurality of prescription-altering inserts is configured to be removably coupled to the bracket and includes at least one archwire insert surface positioned to engage the associated archwire when the associated archwire is received in the archwire passage and when a respective prescription-altering insert is coupled to the bracket;
wherein when one of the plurality of prescription-altering inserts is coupled to the bracket, the at least one archwire insert surface and a subset of the plurality of archwire bracket surfaces define a second prescription to impart a second prescriptive force to the patient's tooth when the bracket is coupled to the patient tooth and when the associated archwire is received in the archwire passage, wherein the second prescriptive force is different than the first prescriptive force.

A2.1 The orthodontic appliance system of paragraph A2, wherein when one of the plurality of prescription-altering inserts is coupled to the bracket, it prevents at least one of the plurality of archwire bracket surfaces from engaging the associated archwire when the associated archwire is received in the archwire passage.

A2.1.1 The orthodontic appliance system of paragraph A2.1, wherein when one of the plurality of prescription-altering inserts is coupled to the bracket, it prevents at least two of the plurality of archwire bracket surfaces from engaging the associated archwire when the associated archwire is received in the archwire passage.

A2.1.2 The orthodontic appliance system of paragraph A2.1, wherein when one of the plurality of prescription-altering inserts is coupled to the bracket, it prevents some but not all of the plurality of archwire bracket surfaces from engaging the associated archwire when the associated archwire is received in the archwire passage.

A2.2 The orthodontic appliance system of any of paragraphs A2-A2.1.2, wherein more than one of the plurality of prescription-altering inserts each define a unique second prescription.

A2.3 The orthodontic appliance system of any of paragraphs A2-A2.2, wherein the system includes any of the various features, structures, portions, components, variations, characteristics, etc, of the systems of any of paragraphs A1-A1.7 (above) and A3-E4 (below).

A2.4 The orthodontic appliance system of any of paragraphs A2-A2.3, wherein the system includes any of the various features, structures, portions, components, variations, characteristics, etc, of the bracket assemblies disclosed herein.

A3 An orthodontic appliance system, comprising:
a bracket adapted to be coupled to a patient's tooth; and
a prescription-altering insert configured to be removably coupled to the bracket;
wherein the bracket defines a first prescriptive archwire passage adapted to receive a first prescriptive force from an associated archwire received within the first prescriptive archwire passage when the bracket is coupled to the patient's tooth and when the prescription-altering insert is not coupled to the bracket;
wherein when the prescription-altering insert is coupled to the bracket, it extends into the first prescriptive archwire passage and with the bracket collectively defines a second prescriptive archwire passage adapted to receive a second prescriptive force from an associated archwire received within the second prescriptive archwire passage; and
wherein the first prescriptive archwire passage and the second prescriptive archwire passage share at least one common surface of the bracket.

A3.1 The orthodontic appliance system of paragraph A3, wherein the first prescriptive archwire passage is defined by a plurality of bracket surfaces, and wherein when the prescription-altering insert is coupled to the bracket, it prevents at least one of the plurality of bracket surfaces from engaging the associated archwire when the associated archwire is received in the second prescriptive archwire passage.

A3.1.1 The orthodontic appliance system of paragraph A3.1, wherein when the prescription-altering insert is coupled to the bracket, it prevents at least two of the plurality of bracket surfaces from engaging the associated archwire when the associated archwire is received in the second prescriptive archwire passage.

A3.1.2 The orthodontic appliance system of paragraph A3.1, wherein when the prescription-altering insert is coupled to the bracket, it prevents some but not all of the plurality of bracket surfaces from engaging the associated archwire when the associated archwire is received in the second prescriptive archwire passage.

A3.2 The orthodontic appliance system of any of paragraphs A3-A3.1.2, further comprising a plurality of prescription-altering inserts, wherein each of the plurality of prescription-altering inserts together with the bracket collectively define a unique second prescriptive archwire passage when the respective prescription-altering insert is coupled to the bracket.

A3.3 The orthodontic appliance system of any of paragraphs A3-A3.2, wherein the second prescriptive force is different than the first prescriptive force.

A3.4 The orthodontic appliance system of any of paragraphs A3-A3.3, wherein the system includes any of the various features, structures, portions, components, variations, characteristics, etc, of the systems of any of paragraphs A1-A2.4 (above) and A4-E4 (below).

A3.5 The orthodontic appliance system of any of paragraphs A3-A3.4, wherein the system includes any of the various features, structures, portions, components, variations, characteristics, etc, of the bracket assemblies disclosed herein.

A4 An orthodontic appliance system, comprising:
a bracket adapted to be coupled to a patient's tooth, wherein the bracket defines a first archwire passage adapted to receive an associated archwire and having a first cross-sectional profile adapted to impart a first prescriptive force on the patient's tooth when the associated archwire is received in the first archwire passage; and
a prescription-altering insert configured to be removably coupled to the bracket, wherein when the prescription-altering insert is coupled to the bracket, the bracket and the prescription-altering insert collectively define a second archwire passage adapted to receive the associated archwire and having a second cross-sectional profile adapted to impart a second prescriptive force on the patient's tooth when the associated archwire is received in the second archwire passage;
wherein the first archwire passage and the second archwire passage share at least one common surface of the bracket.

A4.1 The orthodontic appliance system of paragraph A4, wherein the first archwire passage is defined by a plurality of bracket surfaces, and wherein when the prescription-altering insert is coupled to the bracket, it prevents at least one of the plurality of bracket surfaces from engaging the associated archwire when the associated archwire is received in the second archwire passage.

A4.1.1 The orthodontic appliance system of paragraph A4.1, wherein when the prescription-altering insert is coupled to the bracket, it prevents at least two of the plurality of bracket surfaces from engaging the associated archwire when the associated archwire is received in the second archwire passage.

A4.1.2 The orthodontic appliance system of paragraph A4.1, wherein when the prescription-altering insert is coupled to the bracket, it prevents some but not all of the plurality of bracket surfaces from engaging the associated archwire when the associated archwire is received in the second archwire passage.

A4.2 The orthodontic appliance system of any of paragraphs A4-A4.1.2, further comprising a plurality of prescription-altering inserts, wherein each of the plurality of prescription-altering inserts together with the bracket collectively define a unique second archwire passage when the respective prescription-altering insert is coupled to the bracket.

A4.3 The orthodontic appliance system of any of paragraphs A4-A4.2, wherein the second prescriptive force is different than the first prescriptive force.

A4.4 The orthodontic appliance system of any of paragraphs A4-A4.3, wherein the second cross-sectional profile is different than the first cross-sectional profile.

A4.5 The orthodontic appliance system of any of paragraphs A4-A4.4, wherein the system includes any of the various features, structures, portions, components, variations, characteristics, etc, of the systems of any of paragraphs A1-A3.5 (above) and B-E4 (below).

A4.6 The orthodontic appliance system of any of paragraphs A4-A4.5, wherein the system includes any of the various features, structures, portions, components, variations, characteristics, etc, of the bracket assemblies disclosed herein.

B A self-ligating orthodontic appliance system, comprising:
a base adapted to be coupled to a patient's tooth;
a closure coupled to the base for selective movement relative to the base, wherein the base and the closure collectively define an archwire passage adapted to receive an associated archwire; and
wherein the base and the closure collectively define a connecting assembly configured to movably connect the closure to the base and to permit selective configuration of the orthodontic appliance between an open configuration, in which the archwire passage is configured to permit selective insertion and removal of the associated archwire to and from the archwire passage, and a closed configuration, in which the archwire passage is configured to retain the associated archwire within the archwire passage, wherein the connecting assembly defines a floating hinge that includes:
a pair of male portions; and
a pair of female portions that each define a recess for receiving a respective male portion, wherein the floating hinge is configured so that the male portions are biased toward a nominal position within the recesses when an external lateral force on the closure relative to the base is less than a displacement force, and so that the male portions are translated away from the recesses when the external lateral force on the closure relative to the base is greater than or equal to the displacement force.

B1 The self-ligating orthodontic appliance system of paragraph B, wherein the closure is removably coupled to the base.

B2 The self-ligating orthodontic appliance system of any of paragraphs B-B1, wherein the floating hinge is further configured so that the male portions translate within the recesses but are not forced out of the recesses when the external force on the cap relative to the base is less than a removal force that is greater than the displacement force.

B3 The self-ligating orthodontic appliance system of any of paragraphs B-B2, wherein the male portions each include a cone-shaped projection, and the female portions each include a cone-shaped indentation that define the recesses, wherein when the male portions are in the nominal position, an apex of each cone-shaped projection is engaged with an apex of the respective cone-shaped indentation.

B4 The self-ligating orthodontic appliance system of any of paragraphs B-B3, wherein the base includes the pair of male portions and the cap includes the pair of female portions.

B5 The self-ligating orthodontic appliance system of any of paragraphs B-B3, wherein the base includes the pair of female portions and the cap includes the pair of male portions.

B6 The self-ligating orthodontic appliance system of any of paragraphs B-B4, wherein the system includes any of the various features, portions, components, variations, characteristics, etc. of the systems of any of paragraphs A1-A4.6 (above) and C-E4 (below), including (but not limited to) inclusion of one or more of a ratcheting closure, a prescriptive insert, a ratcheting prescriptive insert, and a non-planar archwire wall or surface.

B7 The self-ligating orthodontic appliance system of any of paragraphs B-B5, wherein the system includes any of the various features, portions, components, variations, characteristics, etc. of the bracket assemblies disclosed herein.

C An orthodontic appliance system, comprising:
  a bracket adapted to be coupled to a patient's tooth; and
  a prescriptive insert adapted to be removably coupled to the bracket in a plurality of prescription-defining positions;
  wherein the bracket and the prescriptive insert collectively define an archwire passage adapted to receive an associated archwire when the insert is coupled to the bracket, wherein each of the plurality of prescription-defining positions each define a unique prescription in which a unique prescription force is applied to the patient's tooth when the bracket is coupled to the patient's tooth and when the associated archwire is received in the archwire passage.

C1 The orthodontic appliance system of paragraph C, wherein each of the plurality of prescription-defining positions respectively defines a unique prescription of the archwire passage, wherein each unique prescription corresponds to a unique prescriptive force that is applied to the patient's tooth when the bracket is coupled to the patient's tooth and when the associated archwire is received in the archwire passage.

C1.1 The orthodontic appliance system of paragraph C1, wherein in response to selective positioning of the insert among the plurality of prescription-defining positions, the unique prescription is selectively adjusted.

C1.2 The orthodontic appliance system of any of paragraphs C-C1.1, wherein the prescriptive insert is configured to be selectively and incrementally translated and/or pivoted into the archwire passage among a range of the plurality of prescription-defining positions.

C1.2.1 The orthodontic appliance system of paragraph C1.2, wherein the unique prescription is based at least in part on an extent into the archwire passage that the prescriptive insert extends.

C2 The orthodontic appliance system of any of paragraphs C-C1.2.1, wherein the system includes any of the various features, portions, components, variations, characteristics, etc. of the systems of any of paragraphs A1-B7 (above) and D-E4 (below), including (but not limited to) inclusion of one or more of a self-ligating feature, a ratcheting closure, a ratcheting prescriptive insert, a non-planar archwire wall or surface, and a floating hinge.

C3 The orthodontic appliance system of any of paragraphs C-C2, wherein the system includes any of the various features, portions, components, variations, characteristics, etc. of the bracket assemblies disclosed herein.

D A self-ligating orthodontic appliance system, comprising:
  a base adapted to be coupled to a patient's tooth; and
  a closure coupled to the base for selective movement relative to the base among a range of prescription-defining positions, wherein the base and the closure collectively define an archwire passage adapted to receive an associated archwire, wherein the closure is adapted to be selectively secured in more than one of the prescription-defining positions, wherein each prescription-defining position defines a unique prescription that corresponds to a unique prescriptive force that is applied to the patient's tooth when the bracket is coupled to the patient's tooth and when the associated archwire is received in the archwire passage.

D1 The self-ligating orthodontic appliance system of paragraph D, wherein the closure is hingedly coupled to the base and is configured to pivot relative to the base in the plurality of positions.

D2 The self-ligating orthodontic appliance system of any of paragraphs D-D1, wherein the system includes any of the various features, portions, components, variations, characteristics, etc. of the systems of any of paragraphs A1-C3 (above) and E-E4 (below), including (but not limited to) inclusion of one or more of a prescriptive insert, a ratcheting prescriptive insert, a non-planar archwire wall or surface, and a floating hinge.

D3 The self-ligating orthodontic appliance system of any of paragraphs D-D2, wherein the system includes any of the various features, portions, components, variations, characteristics, etc. of the bracket assemblies disclosed herein.

E An orthodontic appliance system, comprising:
  a bracket adapted to be coupled to a patient's tooth, wherein the bracket defines an archwire passage configured to receive an associated archwire in a plurality of orientations, wherein each orientation defines a unique prescription for the archwire passage, each unique prescription defined by a unique prescriptive force imparted by the associated archwire on the patient's tooth when the associated archwire is received in the archwire passage and when the bracket is coupled to the patient's tooth.

E1 The orthodontic appliance system of paragraph E, wherein the archwire passage includes at least one non-planar surface configured to engage the associated archwire in more than one of the plurality of orientations.

E2 The orthodontic appliance system of any of any of paragraphs E-E1, wherein the archwire passage includes at least one surface that includes a convex surface extending into the archwire passage.

E2.1 The orthodontic appliance system of paragraph E2, wherein the convex surface includes an apex, and wherein the archwire passage is configured to selectively receive the associated archwire so that it engages the convex surface on either side of the apex.

E3 The orthodontic appliance system of any of paragraphs E-E2.1, wherein the system includes any of the various features, portions, components, variations, characteristics, etc. of the systems of any of paragraphs A1-D3, including (but not limited to) inclusion of one or more of a self-ligating feature, a ratcheting closure, a prescriptive insert, a ratcheting prescriptive insert, a non-planar archwire wall or surface, and a floating hinge.

E4 The orthodontic appliance system of any of paragraphs E-E3, wherein the system includes any of the various features, portions, components, variations, characteristics, etc. of the bracket assemblies disclosed herein.

As used herein, "selective" and "selectively," when modifying an action, movement, configuration, or other activity of one or more components or characteristics of an orthodontic appliance according to the present disclosure, means that the specified action, movement, configuration, or other activity is a direct or indirect result of user manipulation of an aspect of or one or more components of, the appliance, and/or is a direct or indirect result of an action by another component of the appliance. Furthermore, as used herein, the terms "adapted" and "configured" mean that the corresponding component or element is designed and/or implemented to perform the recited function. Thus the use of the terms "adapted" and "configured" should not be construed to mean that the corresponding component or element is simply "capable" of performing or being modified or used to perform a given function, as opposed to being specifically designed or implemented to perform the function.

In the event that any of the references that are incorporated by reference herein define a term in a manner or are otherwise inconsistent with either the non-incorporated disclosure of the present application or with any of the other incorporated references, the non-incorporated disclosure of the present application shall control and the term or terms as used therein only control with respect to the patent document in which the term or terms are defined.

The disclosure set forth above encompasses multiple distinct inventions with independent utility. While each of these inventions has been disclosed in a preferred form or method, the specific alternatives, embodiments, and/or methods thereof as disclosed and illustrated herein are not to be considered in a limiting sense, as numerous variations are possible. The present disclosure includes all novel and non-obvious combinations and subcombinations of the various elements, features, functions, properties, methods and/or steps disclosed herein. Similarly, where any disclosure above or claim below recites "a" or "a first" element, step of a method, or the equivalent thereof, such disclosure or claim should be understood to include one or more such elements or steps, neither requiring nor excluding two or more such elements or steps.

Applicants reserve the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

INDUSTRIAL APPLICABILITY

The orthodontic appliances of the present disclosure are applicable to the orthodontic field.

The invention claimed is:

1. An orthodontic appliance system, comprising:
a self-ligating orthodontic bracket including a plurality of bracket archwire contacting surfaces that define an elongate archwire passage that is configured to receive an archwire, wherein at least one of the bracket archwire contacting surfaces includes a non-planar archwire contacting region that contacts an archwire when an archwire is received into the archwire passage; wherein the self-ligating orthodontic bracket comprises:
a base adapted to be coupled to a patient's tooth; and
a closure coupled to the base for selective movement relative to the base between an open position, in which the closure is coupled to the base and an archwire may be inserted into the archwire passage through an opening of the archwire passage, and a closed position, in which the closure is coupled to the base and the closure obstructs the opening to prevent removal of an archwire from the archwire passage through the opening; and
a prescriptive insert adapted to be removably coupled to the bracket and including an insert archwire contacting surface, wherein when the prescriptive insert is coupled to the bracket, the bracket and prescriptive insert collectively define a first archwire passage configuration, wherein in the first archwire passage configuration, the archwire passage is defined by the plurality of bracket archwire contacting surfaces and the insert archwire contacting surface and imparts a first prescriptive force to an archwire when an archwire is inserted into the archwire passage, wherein when the prescriptive insert is not coupled to the bracket, the plurality of bracket archwire contacting surfaces define a second archwire passage configuration in which a second prescriptive force is imparted to an archwire when an archwire is inserted into the archwire passage;
wherein the first archwire passage configuration is different than the second archwire passage configuration;
wherein the first prescriptive force is different than the second prescriptive force;
wherein the non-planar archwire contacting region contacts an archwire that is received into the archwire passage in the first archwire passage configuration and in the second archwire passage configuration; and
wherein in the first archwire passage configuration and the second archwire passage configuration, a different portion of the non-planar archwire contacting region contacts an archwire that is inserted into the archwire passage.

2. The orthodontic appliance system of claim 1, wherein when the prescriptive insert is coupled to the bracket and an archwire is inserted into the archwire passage, the prescriptive insert prevents at least one of the plurality of bracket archwire contacting surfaces from engaging the archwire, and further wherein when the prescriptive insert is not coupled to the bracket and an archwire is inserted into the archwire passage, the at least one of the plurality of bracket archwire contacting surfaces engages the archwire.

3. The orthodontic appliance system of claim 1, further comprising a plurality of prescriptive inserts each adapted to be removably coupled to the bracket to collectively define with the bracket a unique archwire passage configuration.

4. The orthodontic appliance system of claim 1, wherein the first archwire passage configuration has a different cross-sectional configuration than the second archwire passage configuration.

5. The orthodontic appliance system of claim 1, wherein the non-planar archwire contacting region includes a projection that extends into the archwire passage to engage an archwire that is received into the archwire passage.

6. The orthodontic appliance system of claim 5, wherein the projection includes a convex archwire contacting surface.

7. The orthodontic appliance system of claim 6, wherein the convex archwire contacting surface engages an archwire when an archwire is inserted into the archwire passage in both the first archwire passage configuration and the second archwire passage configuration.

8. The orthodontic appliance system of claim 7, wherein a different portion of the convex archwire contacting surface engages the archwire in the first archwire passage configuration than in the second archwire passage configuration.

9. The orthodontic appliance system of claim 1, wherein the closure defines a closure archwire contacting surface that is configured to contact an archwire when an archwire is received within the archwire passage and the closure is in the closed position.

10. The orthodontic appliance system of claim 9, wherein the closure archwire contacting surface is configured to contact an archwire that is received into the archwire passage when the archwire passage is in the first archwire passage configuration.

11. The orthodontic appliance system of claim 9, wherein the closure archwire contacting surface is configured to contact an archwire that is received into the archwire passage when the archwire passage is in the first archwire passage configuration and when the archwire passage is in the second archwire passage configuration.

12. The orthodontic appliance system of claim 9, wherein when the prescriptive insert is coupled to the bracket, an archwire is received into the archwire passage, and the closure is in the closed position, the prescriptive insert prevents the closure archwire contacting surface from contacting the archwire.

13. The orthodontic appliance system of claim 9, wherein the closure archwire contacting surface includes the non-planar archwire contacting region.

14. The orthodontic appliance system of claim 9, wherein the closure archwire contacting surface is not the non-planar archwire contacting region.

15. The orthodontic appliance system of claim 14, wherein the closure archwire contacting surface includes a non-planar region that contacts an archwire that is received into the archwire passage in at least one of the first and the second archwire passage configurations.

16. The orthodontic appliance system of claim 9, wherein the closure is configured to be selectively configured to and retained in more than one closed position, and wherein a different prescriptive force is imparted to an archwire that is received into the archwire passage when the closure is in each of the closed positions.

17. The orthodontic appliance system of claim 1, wherein the prescriptive insert is removably coupled to the closure of the bracket.

18. The orthodontic appliance system of claim 17, wherein the insert is received within the closure.

19. The orthodontic appliance system of claim 17, wherein the closure of the bracket includes a pair of channels that extend from a facial side of the closure and that include end regions, and further wherein the insert includes a pair of pins that are configured to be received within the pair of channels to couple the insert to the closure.

20. The orthodontic appliance system of claim 1, wherein the closure is coupled to the base by a connecting assembly that defines a floating hinge.

21. The orthodontic appliance system of claim 20, wherein the floating hinge comprises:
a pair of male portions; and
a pair of female portions that each define a recess for receiving a respective male portion, wherein the floating hinge is configured so that the pair of male portions are biased toward a nominal position within each recess when an external lateral force on the closure relative to the base is less than a removal force sufficient to remove the pair of male portions from the recesses defined by the pair of female portions, and so that the pair of male portions are urged back to the nominal position when the pair of male portions are translated away from each recess when the external lateral force on the closure relative to the base is greater than or equal to a displacement force but less than the removal force, and further wherein a distance between the pair of male portions is the same when the pair of male portions is in the nominal position and when the pair of male portions is displaced from the nominal position to a removed position.

22. A self-ligating orthodontic appliance system, comprising:
a base adapted to be coupled to a patient's tooth;
a rigid closure coupled to the base for selective movement relative to the base, wherein the base and the closure collectively define an archwire passage adapted to receive an associated archwire; and
wherein the base and the closure collectively define a connecting assembly configured to movably connect the closure to the base and to permit selective configuration of the orthodontic appliance system between an open configuration, in which the closure is connected to the base and the archwire passage is configured to permit selective insertion and removal of the associated archwire to and from the archwire passage, and a closed configuration, in which the closure is connected to the base and the archwire passage is configured to retain the associated archwire within the archwire passage, wherein the closure has a shape that is the same in both the open configuration and the closed configuration, wherein the connecting assembly defines a floating hinge that includes:
a pair of male portions; and
a pair of female portions that each define a recess for receiving a respective male portion, wherein the floating hinge is configured so that the pair of male portions are biased toward a nominal position within each recess when an external lateral force on the closure relative to the base is less than a removal force sufficient to remove the pair of male portions from the recesses defined by the pair of female portions, and so that the pair of male portions are urged back to the nominal position when the pair of male portions are translated away from each recess when the external lateral force on the closure relative to the base is greater than or equal to a displacement force but less than the removal force, and further wherein a distance between the pair of male portions is the same when the pair of male portions is in the nominal position and when the pair of male portions is displaced from the nominal position to a removed position.

23. The orthodontic appliance system of claim 22, wherein the base and the closure form a self-ligating orthodontic bracket, and further wherein the bracket comprises:
a prescriptive insert adapted to be removably coupled to the bracket and including an insert archwire contacting surface, wherein when the prescriptive insert is coupled to the bracket, the bracket and prescriptive insert collectively define a first archwire passage configuration, wherein in the first archwire passage configuration, the archwire passage is defined by a plurality of bracket archwire contacting surfaces and the insert archwire contacting surface and imparts a first prescriptive force to an archwire when an archwire is inserted into the archwire passage, wherein when the prescriptive insert is not coupled to the bracket, the plurality of bracket archwire contacting surfaces define a second archwire passage configuration in which a second prescriptive force is imparted to an archwire when an archwire is inserted into the archwire passage;
wherein the first archwire passage configuration is different than the second archwire passage configuration; and
wherein the first prescriptive force is different than the second prescriptive force.

24. The orthodontic appliance system of claim 23, wherein at least one of the plurality of bracket archwire contacting surfaces includes a non-planar archwire contacting region that contacts the archwire when the archwire is received into the archwire passage.

25. The orthodontic appliance system of claim 23, wherein the non-planar archwire contacting region contacts an archwire that is received into the archwire passage in the first archwire passage configuration and in the second archwire passage configuration, and wherein in the first archwire passage configuration and the second archwire passage configuration, a different portion of the non-planar archwire contacting region contacts an archwire that is inserted into the archwire passage.

26. The orthodontic appliance system of claim 25, wherein the closure is configured to be selectively configured to and retained in more than one closed position, and wherein a different prescriptive force is imparted to an archwire that is received into the archwire passage when the closure is in each of the closed positions.

27. The orthodontic appliance system of claim 23, wherein when the prescriptive insert is coupled to the bracket and an archwire is inserted into the archwire passage, the prescriptive insert prevents at least one of the plurality of bracket archwire contacting surfaces from engaging the archwire, and further wherein when the prescriptive insert is not coupled to the bracket and an archwire is inserted into the archwire passage, the at least one of the plurality of bracket archwire contacting surfaces engages the archwire.

28. The orthodontic appliance system of claim 23, wherein the closure defines a closure archwire contacting surface that is configured to contact an archwire when an archwire is received within the archwire passage and the closure is in the closed position, and further wherein when the prescriptive insert is coupled to the bracket, an archwire is received into the archwire passage, and the closure is in the closed position, the prescriptive insert prevents the closure archwire contacting surface from contacting the archwire.

29. The orthodontic appliance system of claim 28, wherein the closure archwire contacting surface includes a non-planar region that contacts an archwire that is received into the archwire passage in at least one of the first and the second archwire passage configurations.

30. The orthodontic appliance system of claim 23, wherein the prescriptive insert is removably coupled to the closure of the bracket.

31. The orthodontic appliance system of claim 30, wherein the closure of the bracket includes a pair of channels that extend from a facial side of the closure and that include end regions, and further wherein the insert includes a pair of pins that are configured to be received within the pair of channels to couple the insert to the closure.

* * * * *